(12) United States Patent
Tian et al.

(10) Patent No.: US 9,760,034 B2
(45) Date of Patent: Sep. 12, 2017

(54) RESIN COMPOSITION, THIOPYRAN-BASED SQUARYLIUM COMPOUND AND IMAGE FORMING MATERIAL

(71) Applicant: FUJI XEROX CO., LTD., Tokyo (JP)

(72) Inventors: Minquan Tian, Kanagawa (JP);
Takahiro Ishizuka, Kanagawa (JP);
Makoto Furuki, Kanagawa (JP); Shinji Hasegawa, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 14/499,951

(22) Filed: Sep. 29, 2014

(65) Prior Publication Data

US 2015/0093698 A1   Apr. 2, 2015

(30) Foreign Application Priority Data

Oct. 1, 2013 (JP) ................................. 2013-206605
Aug. 13, 2014 (JP) ................................. 2014-164899

(51) Int. Cl.
| | | |
|---|---|---|
| *G03G 9/00* | (2006.01) | |
| *G03G 9/09* | (2006.01) | |
| *G03G 9/097* | (2006.01) | |
| *C07D 335/02* | (2006.01) | |
| *G02B 1/04* | (2006.01) | |
| *G03G 9/087* | (2006.01) | |

(52) U.S. Cl.
CPC ....... *G03G 9/09775* (2013.01); *C07D 335/02* (2013.01); *G02B 1/04* (2013.01); *G03G 9/08711* (2013.01); *G03G 9/08755* (2013.01)

(58) Field of Classification Search
CPC ..... G03G 9/09775; C07D 335/02; G02B 1/04
USPC ............................ 430/108.4, 108.5; 252/587
See application file for complete search history.

(56) References Cited

U.S. PATENT DOCUMENTS

| | | | | |
|---|---|---|---|---|
| 5,286,604 | A | * | 2/1994 | Simmons, III ......... B41M 5/368 430/199 |
| 5,695,907 | A | | 12/1997 | Chang |
| 2010/0178606 | A1 | * | 7/2010 | Kouyama .......... G03G 9/09733 430/108.4 |
| 2010/0248117 | A1 | * | 9/2010 | Watanabe ............ G03G 9/0819 430/107.1 |

FOREIGN PATENT DOCUMENTS

| | | | |
|---|---|---|---|
| CN | 101762972 A | | 6/2010 |
| JP | 02-118670 A | | 5/1990 |
| JP | 2001-011070 A | | 1/2001 |
| JP | 2002-146254 A | | 5/2002 |
| JP | 2006-297954 A | | 11/2006 |
| WO | 2011/118414 | * | 9/2011 |

OTHER PUBLICATIONS

Machine Transaltion of CN101762972.*
Communication dated Oct. 10, 2016, issued by the State Intellectual Property Office of P.R. China in Chinese application No. 201410520362.3.

* cited by examiner

*Primary Examiner* — Thorl Chea
(74) *Attorney, Agent, or Firm* — Sughrue Mion, PLLC

(57) ABSTRACT

There is provided a resin composition containing an infrared absorber as an inner salt, at least either a carboxylic acid ester or a phosphoric acid ester, and a resin; and an image forming material containing an infrared absorber as an inner salt, at least either a carboxylic acid ester or a phosphoric acid ester, and a thermoplastic resin.

8 Claims, 2 Drawing Sheets

RESIN COMPOSITION, THIOPYRAN-BASED SQUARYLIUM COMPOUND AND IMAGE FORMING MATERIAL

CROSS-REFERENCE TO RELATED APPLICATIONS

This application is based on and claims priority under 35 USC 119 from Japanese Patent Application No. 2013-206605 filed on Oct. 1, 2013 and Japanese Patent Application No. 2014-164899 filed on Aug. 13, 2014.

BACKGROUND

1. Field

The present invention relates to a resin composition, a thiopyran-based squarylium compound and an image forming material.

2. Description of the Related Art

Conventionally, a resin composition and an image forming material each containing an infrared absorber are known.

For example, JP-A-2006-297954 (the term "JP-A" as used herein means an "unexamined published Japanese patent application") discloses a thermal color transfer element comprising a substrate having deposited thereon, in order, (a) a light-to-heat conversion layer, (b) a color transfer layer, and (c) a transparent or translucent, thermally transferable infrared-sensitive adhesive topcoat containing an infrared absorber and a thermoplastic material.

For example, JP-A-2002-146254 discloses an infrared absorbing ink for invisible pattern formation, comprising an infrared absorber having a spectral absorption maximum wavelength at 750 nm to 1,100 nm, whose absorbance at 650 nm is 5% or less of the absorbance at the spectral absorption maximum wavelength.

For example, JP-A-2-118670 discloses a color toner for flash fixing, comprising a core containing a colorant in a binder resin and a cover part containing an infrared absorber in the same resin as the resin above and being provided around the core by heat fusion.

A production method of an infrared absorber is also known.

For example, JP-A-2001-011070 discloses a production method of a chalcogenopyrylium compound, using a compound of substituted acetylenes.

SUMMARY (1) A resin composition containing:
an infrared absorber as an inner salt,
at least either a carboxylic acid ester or a phosphoric acid ester, and
a resin.

DETAILED DESCRIPTION

Figure 1:
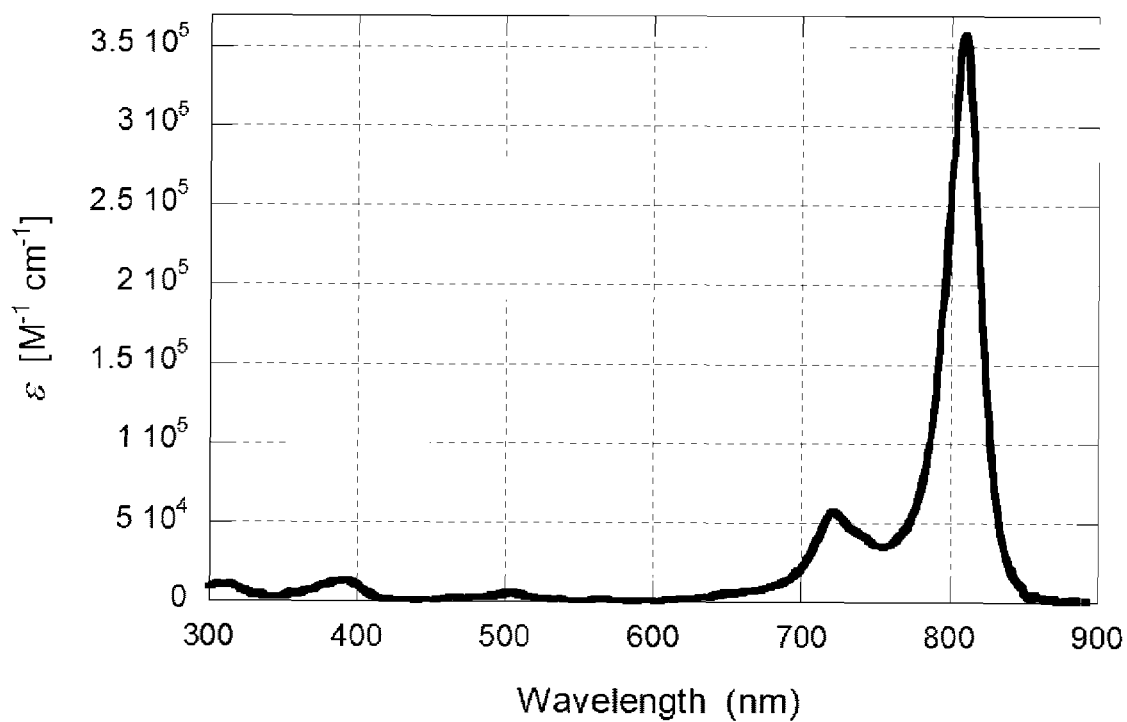
FIG. 1 is a molar extinction coefficient spectrum of a compound where R in formula (1) is a n-butyl group.

The exemplary embodiments of the present invention are described below. The following description and Examples are intended to illustrate the present invention and do not limit the scope of the present invention.

<Resin Composition>

The resin composition according to the exemplary embodiment of the present invention contains an infrared absorber as an inner salt (hereinafter, referred to as "inner salt-type infrared absorber"), at least either a carboxylic acid ester or a phosphoric acid ester, and a resin.

The present inventors have found that when a resin composition containing an inner salt-type infrared absorber further contains a carboxylic acid or a phosphoric acid ester, the composition is excellent in the infrared absorptivity, compared with a case of not containing those esters. A carboxylic acid ester and a phosphoric acid ester had been heretofore sometimes added as a plasticizer to a resin composition but have found to produce an unexpected effect of enhancing the infrared absorption factor of the resin composition.

This effect is produced when the infrared absorber is an inner salt, and when the infrared absorber is not an inner salt, the difference in the infrared absorption factor of the resin composition is small between containing and not containing the above-described esters, failing in showing clear enhancement. Among the compounds known as a plasticizer of a resin composition, even when a compound other than a carboxylic acid ester and a phosphoric acid ester, for example, epoxidized oils/fats (e.g., epoxidized soybean oil, epoxidized linseed oil), is incorporated into a resin composition together with an inner salt-type infrared absorber, the effect above is not obtained. It is probably presumed that an intermolecular interaction of an inner salt-type infrared absorber with a carboxylic acid ester or a phosphoric acid ester contributes to enhancement of the dispersibility of the infrared absorber in a resin and as a result, the infrared absorption factor of the resin composition is improved.

The components of the resin composition according to the exemplary embodiment of the present invention are described in detail below.

[Inner Salt-Type Infrared Absorber]

The infrared absorber as an inner salt (sometimes referred to as "internal salt") has cations and anions in equal numbers inside of the molecule, and the sum total of charges in the molecule is 0.

In view of infrared absorption factor, the inner salt-type infrared absorber preferably has a maximum absorption wavelength ($\lambda_{max}$) in the wavelength range from 800 nm to 1,070 nm.

The inner salt-type infrared absorber includes, for example, a squarylium-based compound, a croconium-based compound, and a naphthalocyanine-based compound, which are inner salts. In terms of high infrared absorption factor and little color turbidity of the compound itself, a squarylium-based compound is preferred. Among others, a compound represented by the following formula (A) and a compound represented by formula (B) are more preferred, and for the reason that an equivalent level of infrared absorption is exhibited at a low content concentration when the molar extinction coefficient is large and the molecular weight is the same, a compound represented by formula (A) is still more preferred.

Incidentally, the color turbidity means that the infrared absorber absorbs light in the visible wavelength region to provide an undesirable color.

—Compound Represented by Formula (A)—

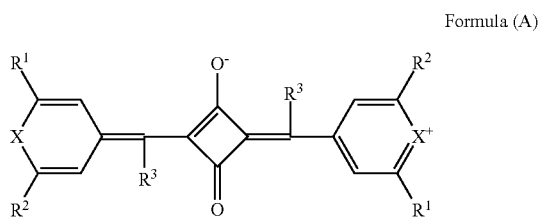

Formula (A)

In formula (A), each of $R^1$ and $R^2$ independently represents an alkyl group or an aryl group, $R^3$ represents a hydrogen atom or an aliphatic group, and X represents an oxygen atom or a sulfur atom.

When at least either $R^1$ or $R^2$ is an aryl group, the maximum absorption wavelength tends to become high, compared with a case where $R^1$ and $R^2$ are alkyl groups. On the other hand, when $R^1$ and $R^2$ are alkyl groups, the molar extinction coefficient tends to become high, compared with a case where at least either $R^1$ or $R^2$ is an aryl group.

The alkyl group represented by $R^1$ and $R^2$ is preferably an alkyl group having a carbon number of 1 to 12, more preferably an alkyl group having a carbon number of 1 to 10, still more preferably an alkyl group having a carbon number of 3 to 8, yet still more preferably an alkyl group having a carbon number of 4 to 6.

The alkyl group represented by $R^1$ and $R^2$ includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decyl group, an isodecyl group, a sec-decyl group, a tert-decyl group, a n-undecyl group, an isoundecyl group, a n-dodecyl group, and an isododecyl group.

In the case where $R^1$ and $R^2$ are alkyl groups, the total of the carbon number of $R^1$ (the carbon number constituting one $R^1$) and the carbon number of $R^2$ (the carbon number constituting one $R^2$) is preferably 6 or more in view of production aptitude and is preferably 12 or less from the viewpoint of high infrared absorption efficiency per unit mass and little color turbidity of the compound itself. The total of the carbon number of $R^1$ and the carbon number of $R^2$ is, in the light of high infrared absorption efficiency per unit mass and little color turbidity of the compound itself, more preferably from 7 to 10, still more preferably from 8 to 10.

As for the carbon number of $R^1$ (the carbon number constituting one $R^1$), in view of production aptitude, high infrared absorption efficiency per unit mass and little color turbidity of the compound itself, the lower limit is preferably 3 or more, more preferably 4 or more, and the upper limit is preferably 8 or less, more preferably 6 or less.

Above all, the carbon number of $R^1$ (the carbon number constituting one $R^1$) is preferably 4 or 5.

The carbon number of $R^2$ (the carbon number constituting one $R^2$) is the same as that of $R^1$.

From the viewpoint of production aptitude, high infrared absorption efficiency per unit mass and little color turbidity of the compound itself, the difference between the carbon number of $R^1$ (the carbon number constituting one $R^1$) and the carbon number of $R^2$ (the carbon number constituting one $R^2$) is preferably smaller and is preferably 1 or 0, more preferably 0.

The aryl group represented by $R^1$ and $R^2$ is preferably a group formed by removing one hydrogen atom from a benzene ring of a benzene or an alkylbenzene, more preferably a group represented by the following structural formula:

In the structural formula above, * represents a bonding site to the central scaffold, and $R^{10}$ represents a hydrogen atom or an alkyl group having a carbon number of 1 to 10. The alkyl group represented by $R^{10}$ is preferably an alkyl group having a carbon number of 2 to 8.

The alkyl group represented by $R^{10}$ includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decyl group, an isodecyl group, a sec-decyl group, and a tert-decyl group.

The alkyl group and aryl group represented by $R^1$ and $R^2$ may be substituted with a halogen atom (e.g., fluorine, chlorine).

From the viewpoint of excellent thermal stability at the time of light energy absorption and associated heat generation of the compound, each of $R^1$ and $R^2$ is independently preferably a n-propyl group, a n-butyl group or a n-pentyl group, and in view of ease of synthesis of the compound, it is more preferred that both are n-propyl groups, both are n-butyl groups, or both are n-pentyl groups.

$R^3$ represents a hydrogen atom or an aliphatic group and is preferably a hydrogen atom.

The aliphatic group may be a chain or a cyclic system. In the case of a chain, the chain may be linear or branched, and in the case of a cyclic system, the cyclic system may be monocyclic or polycyclic.

As the aliphatic group, a saturated hydrocarbon group having a carbon number of 1 to 6, and an unsaturated hydrocarbon group having a carbon number of 2 to 6 are preferred, and an alkyl group having a carbon number of 1 to 6 (preferably a carbon number of 1 to 3, more preferably a carbon number of 1), a cycloalkyl group having a carbon number of 3 to 6 (preferably a carbon number of 3 or 4, more preferably a carbon number of 3), an alkenyl group having a carbon number of 2 to 6 (preferably a carbon number of 2 or 3, more preferably a carbon number of 2), and a cycloalkenyl group having a carbon number of 3 to 6 (preferably a carbon number of 3 or 4, more preferably a carbon number of 3) are more preferred.

The alkyl group includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, and a tert-hexyl group.

The cycloalkyl group includes, for example, a cyclopropyl group, a cyclobutyl group, a cyclopentyl group, and a cylohexyl group.

The alkenyl group includes, for example, an ethenyl group, a propenyl group, a butenyl group, a pentenyl group, and a hexenyl group.

The cycloalkenyl group includes, for example, a cyclopropenyl group, a cyclobutenyl group, a cyclopentenyl group, and a cyclohexenyl group.

X represents an oxygen atom or a sulfur atom and is preferably a sulfur atom.

Specific examples of the compound represented by formula (A) include, for example, the following Compounds A-01 to A-30.

A-01

A-02

A-03

A-04

A-05

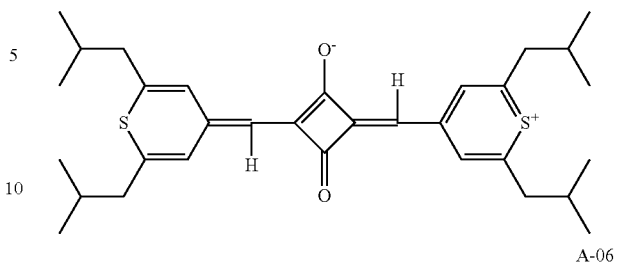

A-06

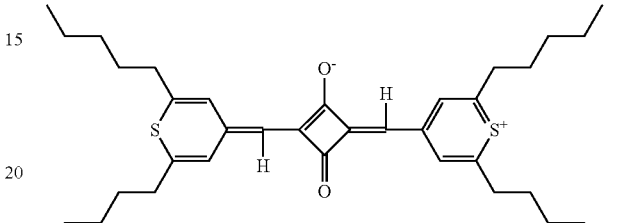

A-07

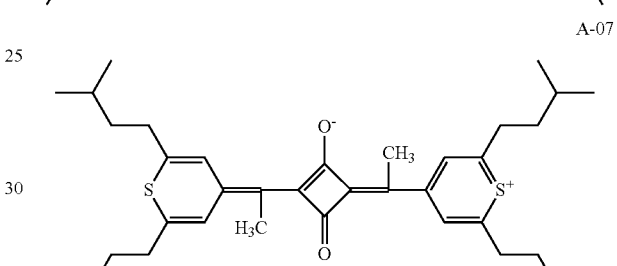

A-08

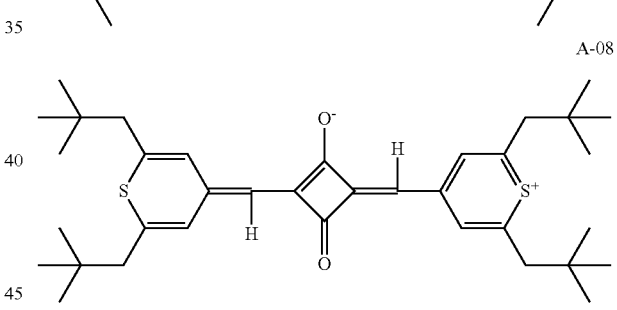

A-09

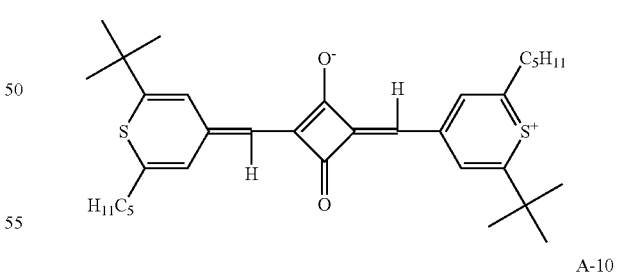

A-10

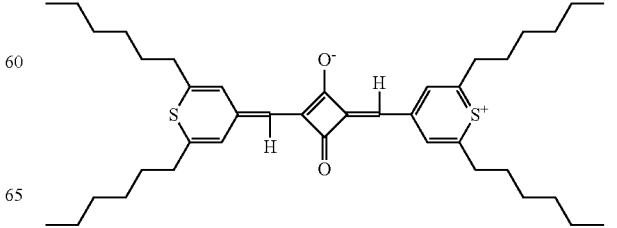

A-11
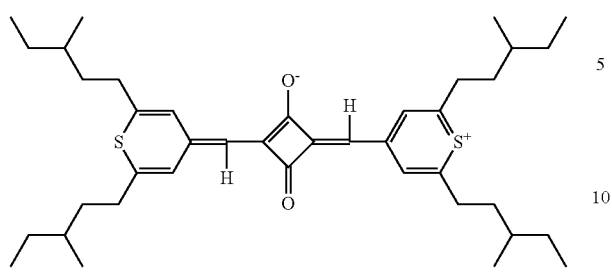
A-12
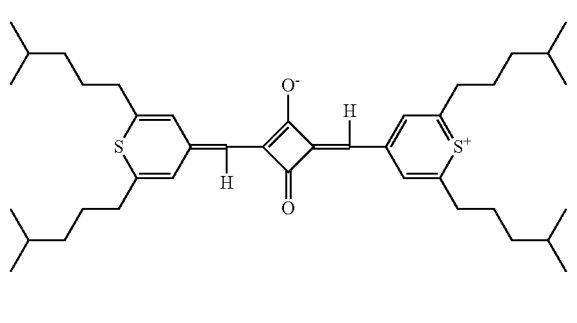 [SMILES: CCCCCC1=CC(=CC2=C([O-])/C(=C/c3cc(CCCCC)[s+]c(CCCCC)c3)C2=O)C=C(CCCCC)S1]
A-13
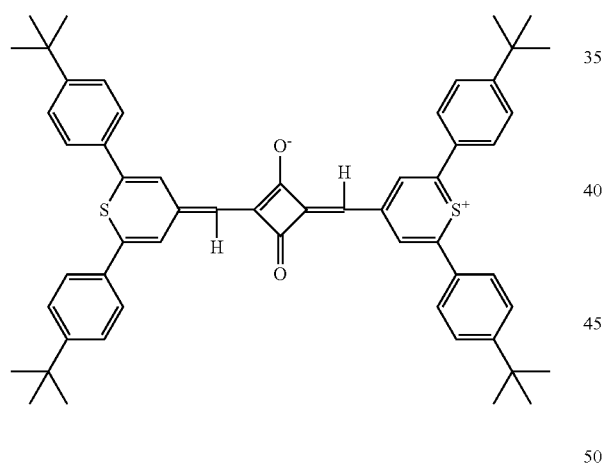
A-14
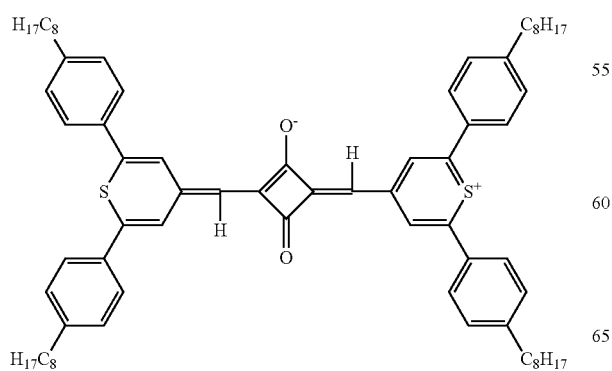
A-15
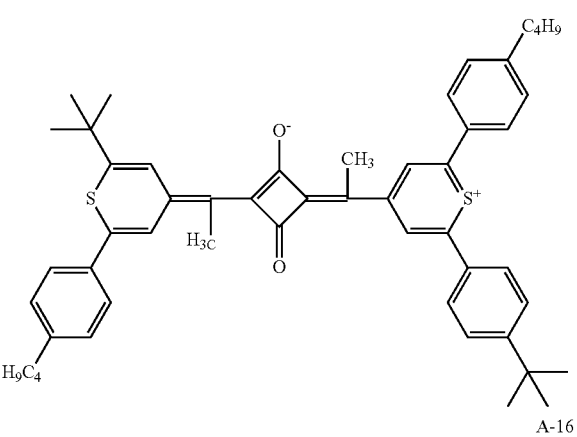
A-16
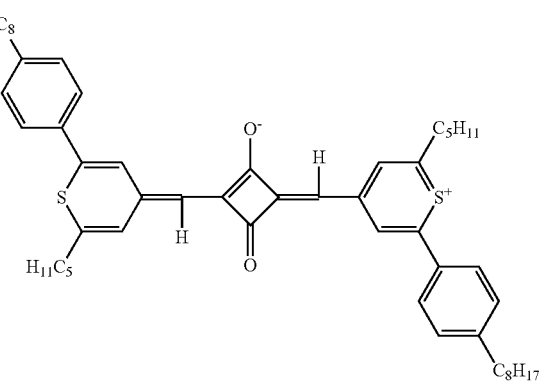
A-17
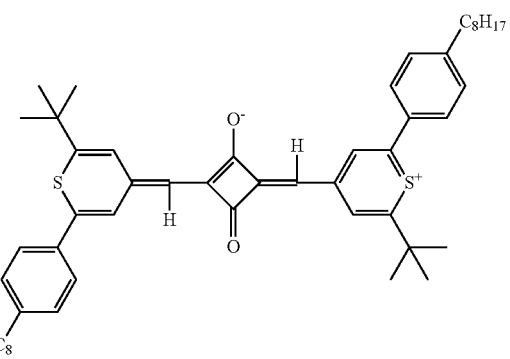
A-18
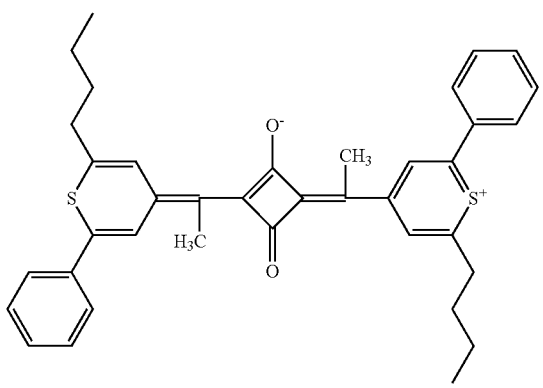

-continued
A-19
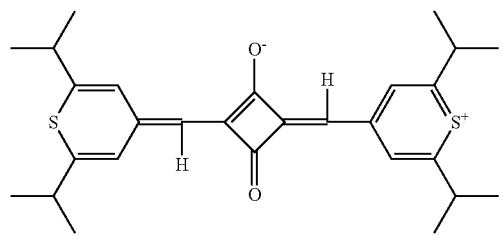 [SMILES: CC(C)C1=CC(=CC2=C([O-])/C(=C/c3cc(C(C)C)[s+]c(C(C)C)c3)C2=O)C=C(C(C)C)S1]
A-20
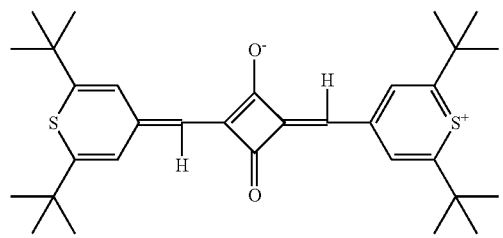 [SMILES: CC(C)(C)C1=CC(=CC2=C([O-])/C(=C/c3cc(C(C)(C)C)[s+]c(C(C)(C)C)c3)C2=O)C=C(C(C)(C)C)S1]
A-21
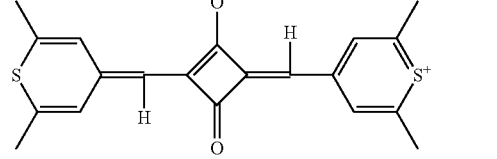
A-22
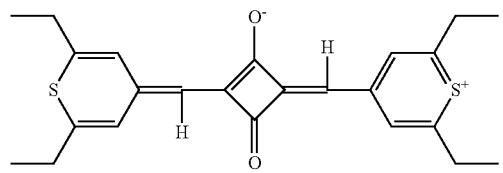
A-23
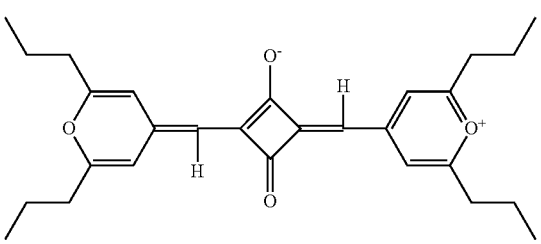
A-24
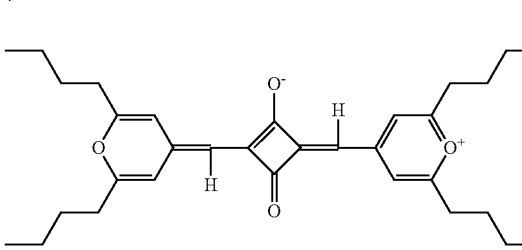
A-25
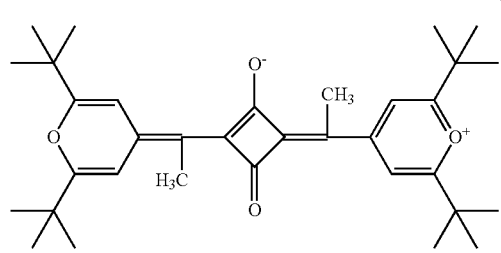
-continued
A-26
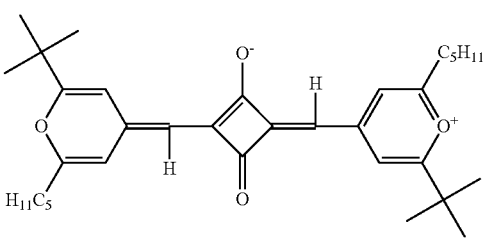
A-27
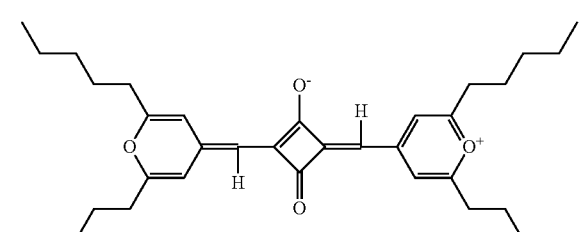
A-28
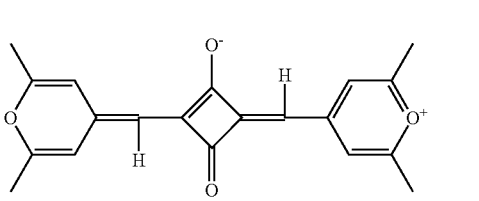
A-29
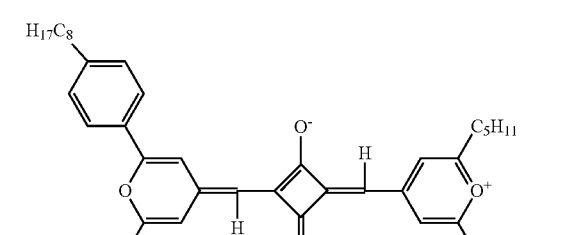
A-30
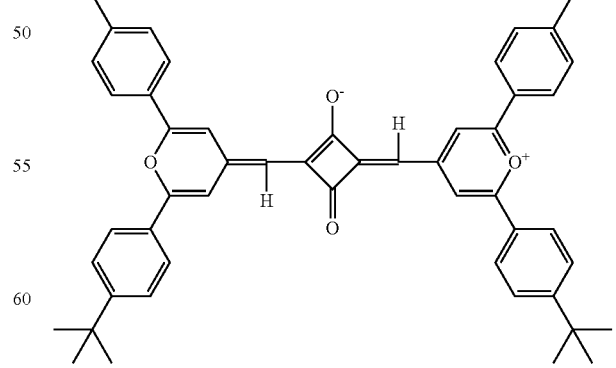
The compound represented by formula (A) can be synthesized, for example, by the synthesis method described in JP-A-2001-11070, JP-A-2006-251755, etc.

—Compound Represented by Formula (1)—

Among the compounds represented by formula (A), a thiopyran-based squarylium compound represented by the following formula (1) is excellent in the thermal stability at the time of light energy absorption and associated heat generation.

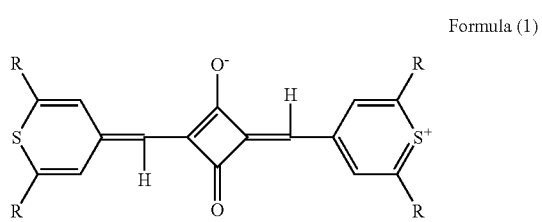

Formula (1)

In formula (1), R represents a n-propyl group, a n-butyl group or a n-pentyl group. That is, the thiopyran-based squarylium compound represented by formula (1) includes the compounds represented by the following structural formulae. These are Compounds A-04, A-01 and A-06 illustrated above.

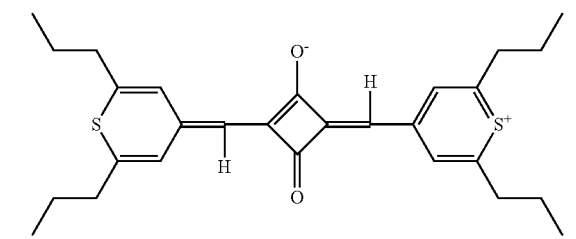

Molecular weight: 466.7
$\lambda_{max}$: 809nm
$\varepsilon_{max}$: 3.60 × 10$^5$ M$^{-1}$cm$^{-1}$

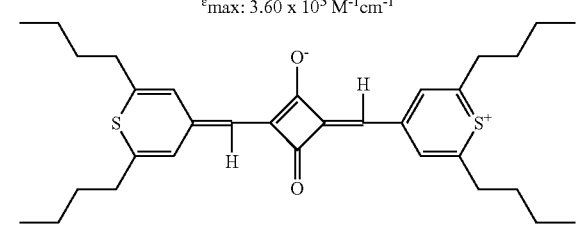

Molecular weight: 522.8
$\lambda_{max}$: 810nm
$\varepsilon_{max}$: 3.58 × 10$^5$ M$^{-1}$cm$^{-1}$

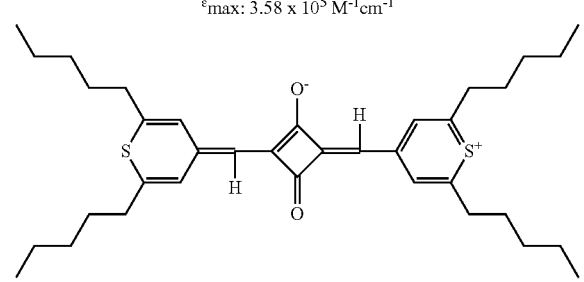

Figure 2:
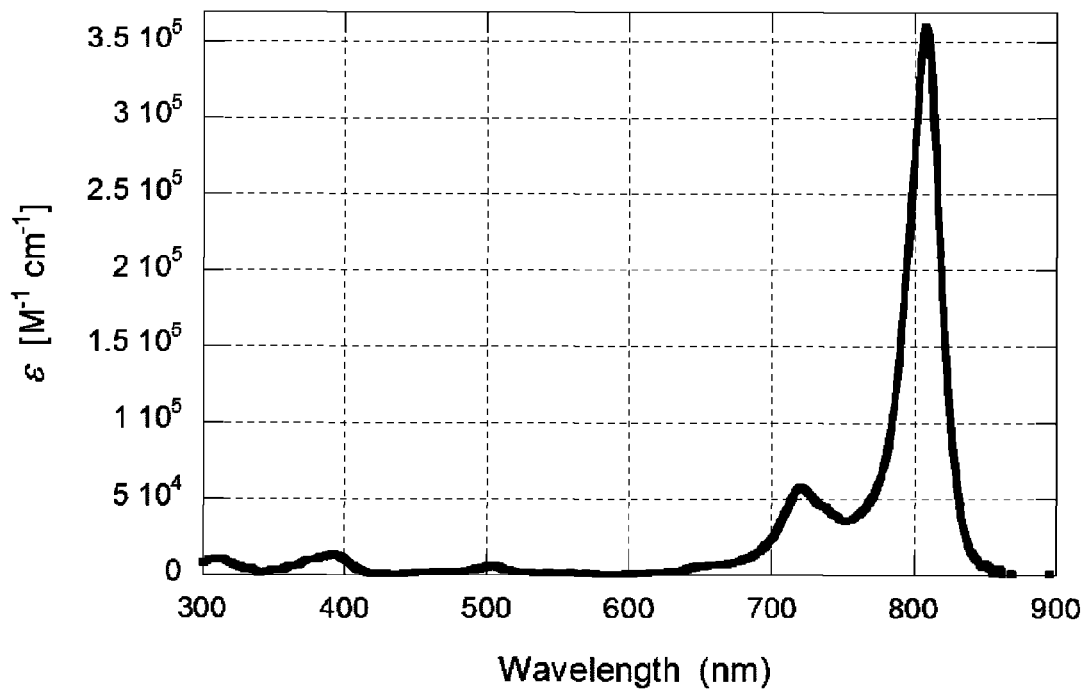
FIG. 2 is a molar extinction coefficient spectrum of a compound where R in formula (1) is a n-propyl group.
Figure 3:
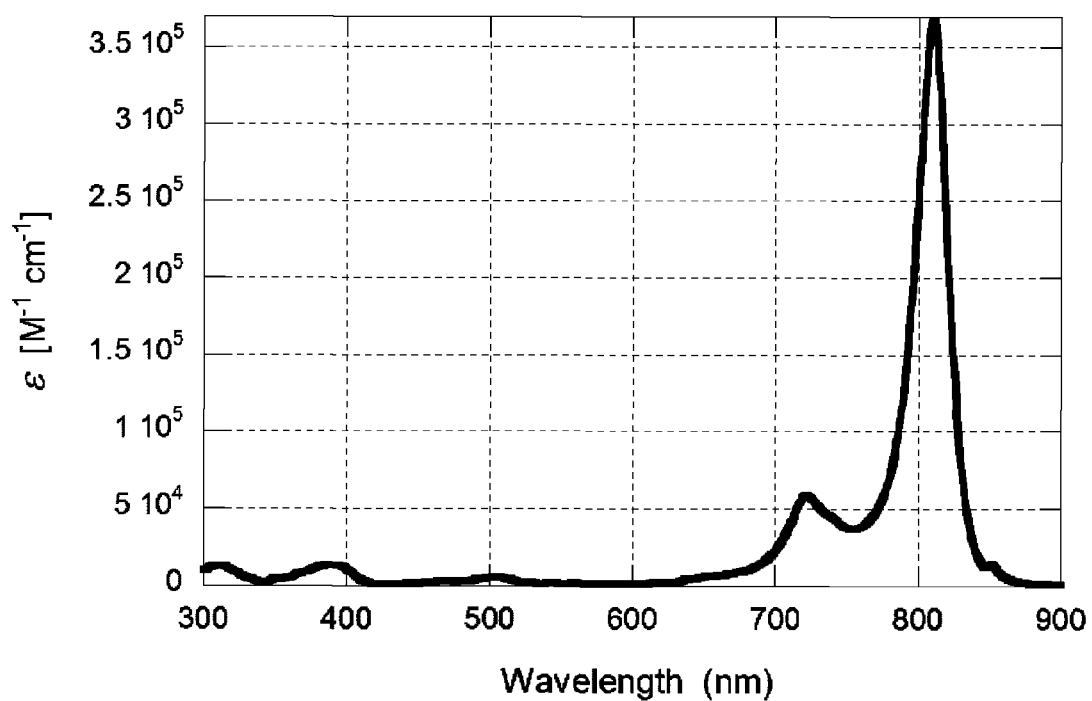
FIG. 3 is a molar extinction coefficient spectrum of a compound where R in formula (1) is a n-pentyl group.

Molecular weight: 578.9
$\lambda_{max}$: 810nm
$\varepsilon_{max}$: 3.68 × 10$^5$ M$^{-1}$cm$^{-1}$ FIGS. 1 to 3 show the molar extinction coefficient of the compound represented by formula (1) (FIG. 1: R in formula (1) is a n-butyl group, FIG. 2: R in formula (1) is n n-propyl group, FIG. 3: R in formula (1) is a n-pentyl group). The compound represented by formula (1) has a maximum absorption wavelength ($\lambda_{max}$) near a wavelength of 810 nm, in which the molar extinction coefficient ($\varepsilon_{max}$) at the maximum absorption wavelength is large and the absorption factor of visible light is low. Accordingly, the compound represented by formula (1) is excellent in the infrared absorptivity and invisibility and is suitably used as an infrared absorber.

In addition, the compound represented by formula (1) is excellent in the thermal stability at the time of light energy absorption and associated heat generation and can be hardly decomposed by the irradiation with light energy. Therefore, according to the compound represented by formula (1), an infrared absorber excellent in the thermal stability at the time of light energy absorption and associated heat generation and resistant to decomposition upon irradiation with light energy and to generation of a volatile sulfur compound, is provided.

When the compound represented by formula (1) is used as an infrared absorber in an optical fixing-type image forming material such as optical fixing toner, the compound is hardly decomposed at the time of optical fixing of the image forming material, and a volatile sulfur compound is less generated from the image forming material and an image after fixing. The volatile sulfur compound is a substance of which load in vivo or on the environment is concerned, and therefore, it is important in practice that a volatile sulfur compound is less likely to occur at the time of optical fixing of an optical fixing-type image forming material and generation of a volatile sulfur compound from an image after optical fixing is suppressed.

The compound represented by formula (1) is believed to be excellent in the thermal stability at the time of light energy absorption and associated heat generation by virtue of the configuration where the substituent at the R position of formula (1) is a linear alkyl group having a carbon number of 3 to 5. It is considered that if the substituent at the R position is a branched alkyl group or an alkyl group having a carbon number of 6 or more, the intermolecular interaction is weakened due to bulkiness of the substituent and the compound is more likely to thermally decompose than the compound represented by formula (1). On the other hand, if the substituent at the R position is an alkyl group having a carbon number of 2 or less, the cohesive force between molecules is strong and the grindability is inferior to that of the compound represented by formula (1), resulting in poor handleability in use for an image forming material.

—Compound Represented by Formula (B)—

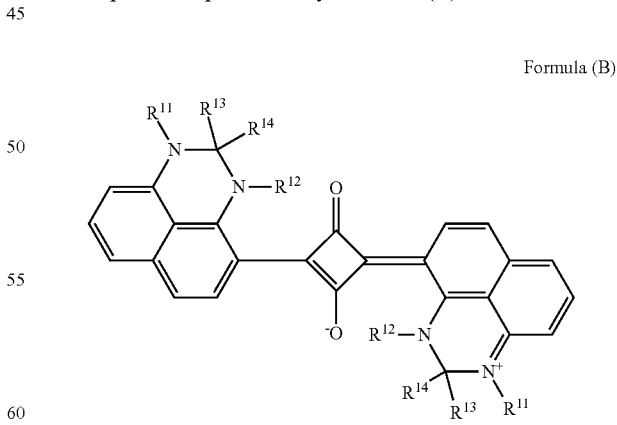

Formula (B)

In formula (B), each of $R^{11}$ and $R^{12}$ independently represents a hydrogen atom or a methyl group, and each of $R^{13}$ and $R^{14}$ independently represents an alkyl group having a carbon number of 1 to 12. $R^{13}$ and $R^{14}$ may combine to form a ring. The alkyl group represented by $R^{13}$ and $R^{14}$ is preferably an alkyl group having a carbon number of 2 to 8.

The alkyl group represented by $R^{13}$ and $R^{14}$ includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, and a tert-octyl group.

The alkyl group represented by $R^{13}$ and $R^{14}$ may be substituted with a halogen atom (e.g., fluorine, chlorine).

Specific examples of the compound represented by formula (B) include, for example, the following Compounds B-01 to B-06.

B-01

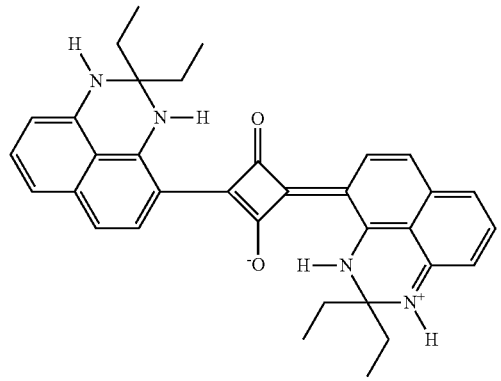

B-02

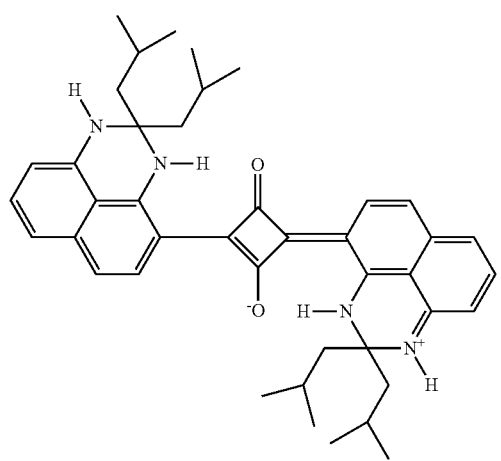

B-03

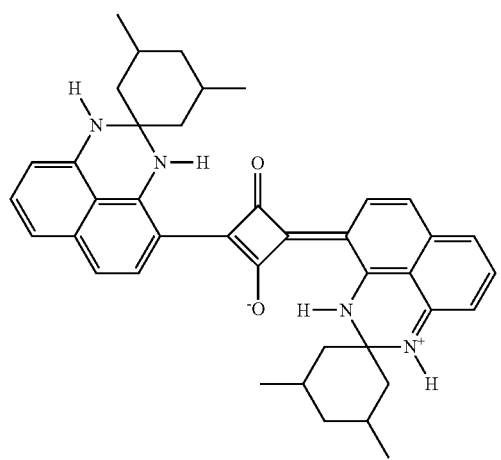

B-04

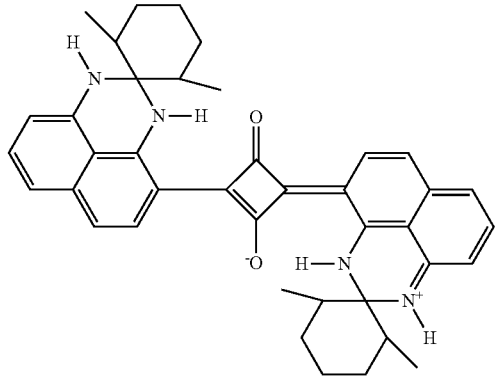

B-05

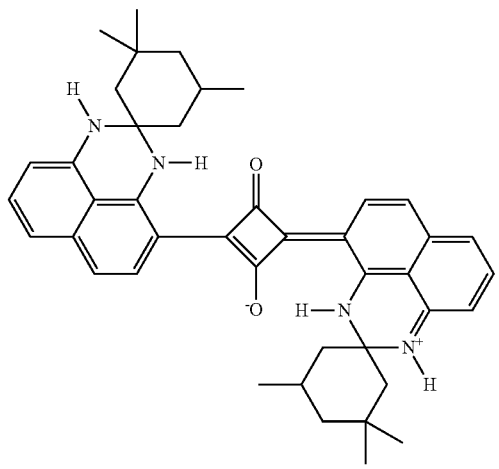

B-06

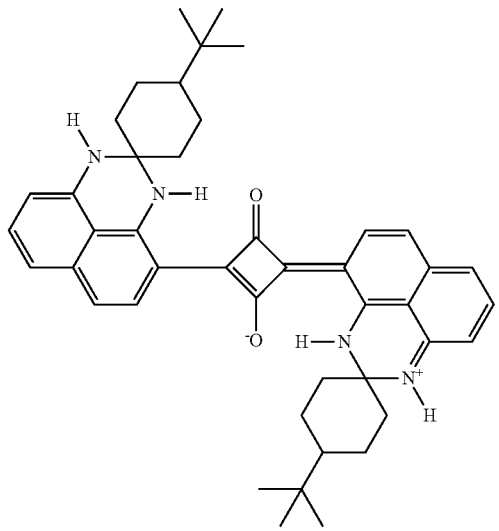

The compound represented by formula (B) can be synthesized, for example, by the synthesis method described in JP-A-2010-077261, JP-A-2010-186014, JP-A-2011-039359, etc.

The resin composition may contain an infrared absorber that is not an inner salt, but from the standpoint of suppressing generation of color turbidity, it is preferable not to contain such an infrared absorber. The infrared absorber that is not an inner salt includes, for example, conventionally known infrared absorbers such as cyanine-based compound and aminium-based compound.

[Carboxylic Acid Ester, Phosphoric Acid Ester]

The resin composition according to the exemplary embodiment of the present invention contains at least one ester selected from a carboxylic acid ester and a phosphoric acid ester. The carboxylic acid ester and phosphoric acid ester include, for example, the following compounds.

—Carboxylic Acid Ester—

The carboxylic acid ester includes, for example, an ester of a monovalent or polyvalent carboxylic acid and a monohydric alcohol, and is preferably an ester of a monovalent, divalent or trivalent carboxylic acid and a monohydric alcohol, more preferably an ester of a divalent or trivalent carboxylic acid and a monohydric alcohol.

The monovalent carboxylic acid includes, for example, a fatty acid, and among others, a fatty acid with the hydrocarbon group having a carbon number of 3 to 12 (preferably from 3 to 10, more preferably from 6 to 10, still more preferably from 8 to 10) is preferred. Specific examples thereof include a propanoic acid, a butanoic acid, a pentanoic acid, a hexanoic acid, a heptanoic acid, an octanoic acid, a nonanoic acid, a decanoic acid, an undecanoic acid, and a dodecanoic acid.

The divalent or trivalent carboxylic acid includes a phthalic acid, an adipic acid, a sebacic acid, a citric acid, an acetylated citric acid, a trimellitic acid, an azelaic acid, a suberic acid, a pimelic acid, a glutaric acid, a succinic acid, a malonic acid, an oxalic acid, a fumaric acid, a maleic acid, an isophthalic acid, a terephthalic acid, a 1,2,3-propanetricarboxylic acid, a cyclohexane-1,2,4-tricarboxylic acid, a 1,3,5-benzenetricarboxylic acid, etc.

From the standpoint of further enhancing the infrared absorption factor of the resin composition, the monohydric alcohol is preferably a monohydric alcohol having a carbon number of 3 to 12, more preferably a monohydric alcohol having a carbon number of 3 to 10, still more preferably a monohydric alcohol having a carbon number of 6 to 10, yet still more preferably monohydric alcohol having a carbon number of 8 to 10. This monohydric alcohol may be linear or branched but is preferably linear. Preferred monohydric alcohols include, for example, 1-decanol, 8-methyl-1-nonanol, 1-nonanol, 7-methyl-1-octanol, 1-octanol, 6-methyl-1-heptanol, and 2-ethyl-1-hexanol.

The carboxylic acid ester specifically includes a phthalic acid ester such as di(2-ethylhexyl) phthalate (DEHP), diisodecyl phthalate (DIDP), diisononyl phthalate (DINP), dinonyl phthalate (DNP) and dibutyl phthalate (DBP); an adipic acid ester such as di(2-ethylhexyl) adipate (DEHA), diisodecyl adipate (DIDA), diisononyl adipate (DINA) and dinonyl adipate (DNA); a sebacic acid ester such as di(2-ethylhexyl) sebacate (DEHS) and diisopropyl sebacate (DIPS); a trimellitic acid ester such as tris(2-ethylhexyl) trimellitate (TOTM); a citric acid ester such as tributyl acetylcitrate (ATBC); a succinic acid ester such as di(2-ethylhexyl) succinate; a fatty acid ester such as (2-ethylhexyl) propanoate, isodecyl propanoate, isononyl propanoate, nonyl propanoate, butyl propanoate, (2-ethylhexyl) octanoate, isodecyl octanoate, isononyl octanoate, nonyl octanoate, butyl octanoate, (2-ethylhexyl) dodecanoate, isodecyl dodecanoate, isononyl dodecanoate, nonyl dodecanoate and butyl dodecanoate; a 1,2,3-propanetricarboxylic acid ester such as trihexyl 1,2,3-propanetricarboxylate; a 1,3,5-benzenetricarboxylic acid ester such as tris(2-ethylhexyl) 1,3,5-benzenetricarboxylate; etc.

Examples of the carboxylic acid ester are illustrated below, but the present invention is not limited thereto.

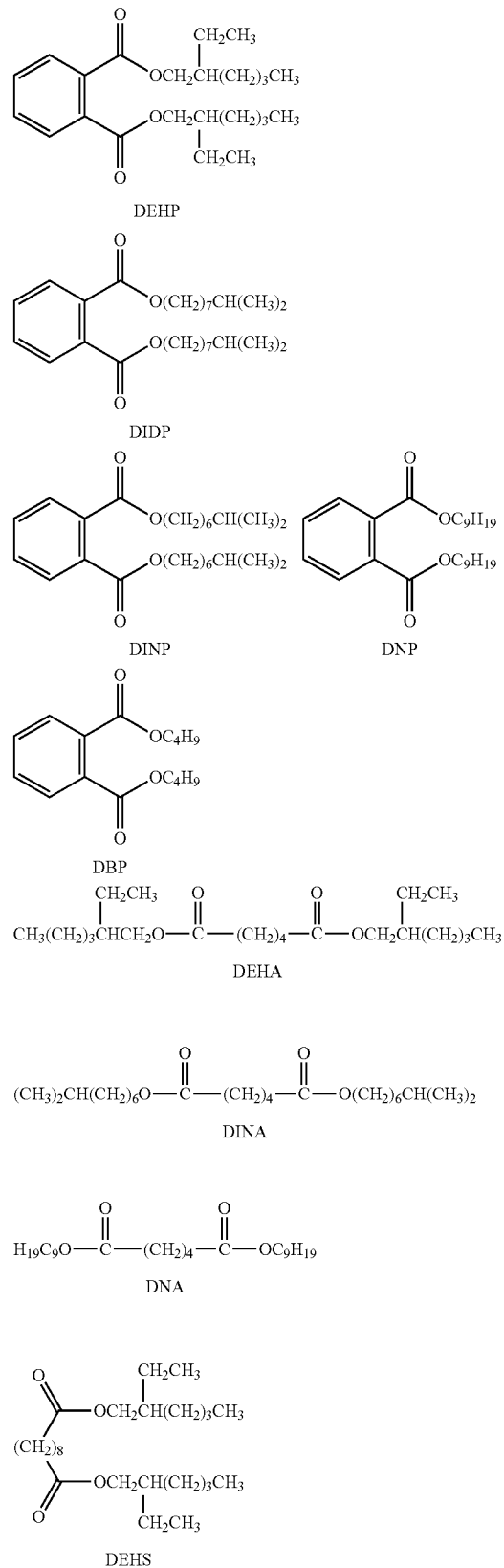

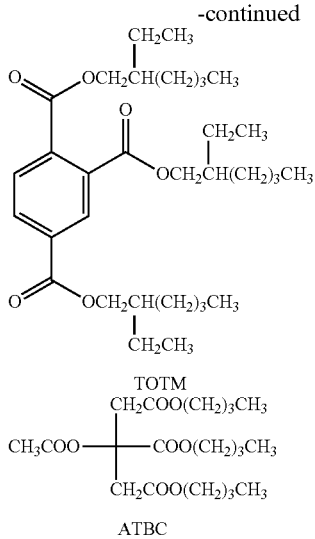

TOTM

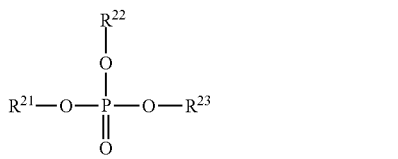

ATBC

—Phosphoric Acid Ester—

The phosphoric acid ester includes, for example, a compound represented by the following formula (P):

$$R^{21}-O-\underset{\underset{O}{\overset{O}{\|}}}{\overset{O-R^{22}}{P}}-O-R^{23}$$

Formula (P)

In formula (P), each of $R^{21}$, $R^{22}$ and $R^{23}$ independently represents an alkyl group or an aryl group.

The alkyl group represented by $R^{21}$, $R^{22}$ and $R^{23}$ is preferably an alkyl group having a carbon number of 1 to 12, more preferably an alkyl group having a carbon number of 1 to 8, still more preferably an alkyl group having a carbon number of 1 to 6, yet still more preferably an alkyl group having a carbon number of 3 to 6.

The alkyl group represented by $R^{21}$, $R^{22}$ and $R^{23}$ may be linear or branched and is preferably branched.

The alkyl group represented by $R^{21}$, $R^{22}$ and $R^{23}$ includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decyl group, an isodecyl group, a sec-decyl group, a tert-decyl group, a n-undecyl group, an isoundecyl group, a n-dodecyl group, and an isododecyl group.

The aryl group represented by $R^{21}$, $R^{22}$ and $R^{23}$ is preferably a group formed by removing one hydrogen atom from a benzene ring of a benzene or an alkylbenzene, more preferably a group represented by the following structural formula:

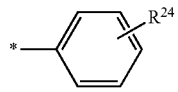

In the structural formula above, * represents a bonding site to an oxygen atom, and $R^{24}$ represents a hydrogen atom or an alkyl group having a carbon number of 1 to 6 and is preferably an alkyl group having a carbon number of 1 to 4. The alkyl group represented by $R^{24}$ includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a sec-hexyl group, and a tert-hexyl group.

The alkyl group and aryl group represented by $R^{21}$, $R^{22}$ and $R^{23}$ may be substituted with a halogen atom (e.g., fluorine, chlorine).

The phosphoric acid ester specifically includes tricresyl phosphate (TCP), triphenyl phosphate (TPP), (2-ethylhexyl) diphenyl phosphate (EHDPP), tris(2-ethylhexyl) phosphate (TEHP), triamyl phosphate (TAP), tributyl phosphate (TBP), triethyl phosphate (TEP), trimethyl phosphate (TMP), etc.

Examples of the phosphoric acid ester are illustrated below, but the present invention is not limited thereto.

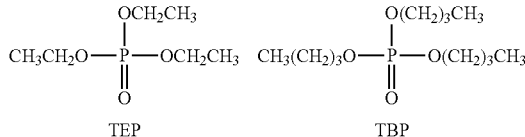

TEP      TBP

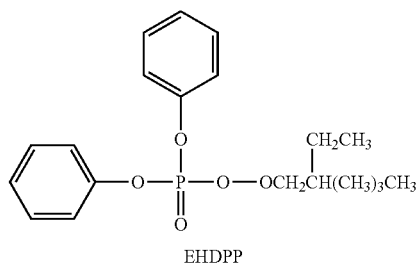

TAP

EHDPP

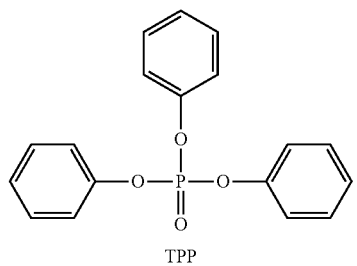

TPP

-continued

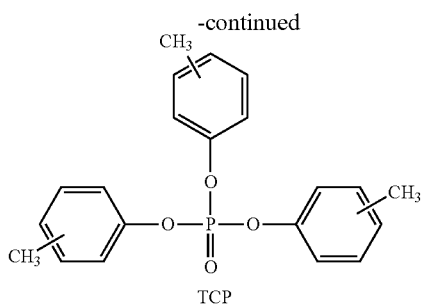
TCP

In the resin composition according to the exemplary embodiment of the present invention, the ratio between the total amount of the carboxylic acid ester and the phosphoric acid ester and the total amount of the inner salt-type infrared absorbers (carboxylic acid ester and phosphoric acid ester/inner salt-type infrared absorbers, mass ratio) is preferably from 1/10 to 10, more preferably from 1/5 to 5, still more preferably from 1/2 to 2.

[Resin]

The resin contained in the resin composition according to the exemplary embodiment of the present invention is not limited in its kind and may be selected, for example, from a thermoplastic resin, a thermosetting resin and a photocurable resin, according to the usage of the resin composition. One resin may be used alone, or two or more resins may be used in combination.

[Other Component]

The resin composition according to the exemplary embodiment of the present invention may contain other components according to the purpose. Other components include various known additives, for example, a viscosity regulator, a pH adjuster, an antioxidant, an antiseptic, a fungicide, an organic solvent, and a pigment.

[Production Method of Resin Composition]

The production method of the resin composition according to the exemplary embodiment of the present invention is not particularly limited and includes, for example, a method where a resin, an infrared absorber, at least either a carboxylic acid ester or a phosphoric acid ester (referred to as "esters"), and other components are dissolved or dispersed in a solvent; a method where a resin is dispersed in a solution to form a particle and an infrared absorber, esters and other materials are added thereto and cohered together; a method where a monomer of the material of the resin is polymerized in a solution in which an infrared absorber, esters and other materials are present together; and when the resin is a thermoplastic resin, a method where a resin, an infrared absorber, esters and other materials are melt-kneaded and then subjected to forming or pulverization.

[Usage of Resin Composition]

The usage of the resin composition according to the exemplary embodiment of the present invention is not particularly limited and includes, for example, an image forming material such as electrophotographic toner and infrared absorbing ink; a coating material for a heating element that generates heat by the absorption of an infrared ray; and a filter membrane-forming composition for an infrared filter that transmits visible light and blocks an infrared ray. The resin composition according to the exemplary embodiment of the present invention may the above-described material or composition itself or may be an intermediate composition for the production thereof.

<Image Forming Material>

The image forming material according to the exemplary embodiment of the present invention contains an inner salt-type infrared absorber, at least either a carboxylic acid ester or a phosphoric acid ester, and a thermoplastic resin.

The image forming material includes, for example, an electrophotographic toner and an infrared absorbing ink. The electrophotographic toner includes, for example, an optical fixing toner and an invisible toner. The infrared absorbing ink includes, for example, an ink for an inkjet printer; and an ink for printing such as letterpress printing, offset printing, flexo printing, gravure printing and silk printing.

According to the image forming material in the exemplary embodiment of the present invention, the infrared absorptivity is excellent, compared with a case of not containing a carboxylic acid ester and a phosphoric acid ester, and in turn, the fixability to a recording medium by infrared irradiation is excellent.

Also, according to the image forming material in the exemplary embodiment of the present invention, the amount of the infrared absorber necessary to ensure the fixability to a recording medium can be decreased, compared with a case of not containing a carboxylic acid ester and a phosphoric acid ester, so that the color turbidity can be reduced and the cost can be driven down.

[Inner Salt-Type Infrared Absorber]

The inner salt-type infrared absorber contained in the image forming material according to the exemplary embodiment of the present invention has the same meaning as the inner salt-type infrared absorber contained in the resin composition according to the exemplary embodiment of the present invention, and its preferred embodiment is also the same. In the image forming material according to the exemplary embodiment of the present invention, the inner salt-type infrared absorber absorbs an infrared ray and generates heat.

The compound represented by formula (A) and the compound represented by formula (B), particularly, the compound represented by formula (A), have low absorbance in the visible wavelength region and therefore, when applied to an image forming material, are less likely to offer the color from the infrared absorber. Accordingly, in the case where the image forming material further contains a pigment, an image forming material preserving the color from the pigment is provided, and in the case where the image forming material is an invisible toner, an invisible toner excellent in the invisibility is provided. Incidentally, the "invisibility" as used in the description of the present invention means to be hardly recognized with the human eye, and it is ideal not to be recognized at all (invisible).

The compound represented by formula (A) and the compound represented by formula (B), particularly, the compound represented by formula (A), have a maximum absorption wavelength in the range of 810 nm or more giving good laser emission efficiency and have a high infrared absorption factor, thus such a compound can be used at a low concentration in the resin composition and in turn, be less likely to affect the color of the image forming material or the invisibility of the invisible toner.

In the image forming material according to the exemplary embodiment of the present invention, the total amount of the inner salt-type infrared absorbers is preferably from 0.05 parts by mass to 20 parts by mass, more preferably from 0.1 parts by mass to 10 parts by mass, per 100 parts by mass of the thermoplastic resin.

The image forming material may contain an infrared absorber that is not an inner salt, but from the standpoint of suppressing the generation of color turbidity, it is preferable not to contain such an infrared absorber.

[Carboxylic Acid Ester, Phosphoric Acid Ester]

The carboxylic acid ester and phosphoric acid ester contained in the image forming material according to the exemplary embodiment of the present invention have the same meanings as the carboxylic acid ester and phosphoric acid ester contained in the resin composition according to the exemplary embodiment of the present invention, and preferred embodiments thereof are also the same.

In the image forming material according to the exemplary embodiment of the present invention, the total amount of the carboxylic acid ester and the phosphoric acid ester is preferably from 0.05 parts by mass to 20 parts by mass, more preferably from 0.1 parts by mass to 10 parts by mass, per 100 parts by mass of the thermoplastic resin.

In the image forming material according to the exemplary embodiment of the present invention, the ratio between the total amount of the carboxylic acid ester and the phosphoric acid ester and the total amount of the inner salt-type infrared absorbers (carboxylic acid ester and phosphoric acid ester/inner salt-type infrared absorbers, mass ratio) is preferably from $1/10$ to 10, more preferably from $1/5$ to 5, still more preferably from $1/2$ to 2.

[Thermoplastic Resin]

The thermoplastic resin is softened or melted by heating and thereafter, again solidified to fix the image forming material on a recording medium. The image forming material according to the exemplary embodiment of the present invention contains a thermoplastic resin and therefore, can be fixed with less light energy, compared with a case of not containing a thermoplastic resin.

The thermoplastic resin includes, for example, a thermoplastic resin composed of a naturally occurring polymer, and a thermoplastic resin composed of a synthetic polymer. The thermoplastic resin specifically includes, for example, a polyester resin, an epoxy resin, a styrene-acrylic resin, a polyamide resin, a polyvinyl resin, a polyolefin resin, a polyurethane resin, a polybutadiene resin, a poly(alkyl methacrylate) resin, an acrylic resin, and a polystyrene resin. As the thermoplastic resin, one resin may be used alone, or two or more resins may be used in combination.

Among these thermoplastic resins, in view of thermal fixing efficiency, a polyester resin and a styrene-acrylic resin are preferred, and a polyester resin is more preferred.

The weight average molecular weight of the thermoplastic resin is preferably from 1,000 to 100,000, more preferably from 5,000 to 50,000. When the weight average molecular weight is 1,000 or more, a problem such as offset or fusion is less likely to occur, and when the weight average molecular weight is 100,000 or less, the amount of heat necessary for fixing is not excessively large, and the image forming material is efficiently fixed by the irradiation with light.

The glass transition temperature of the thermoplastic resin is preferably from 50° C. to 150° C. When the glass transition temperature is in the range above, compared with a case where the glass transition temperature is outside the range above, the thermoplastic resin is softened or melted with an appropriate amount of heat and thereafter, again solidified to fix the image-forming material on a recording medium. The glass transition temperature of the thermoplastic resin is more preferably from 55° C. to 70° C.

[Colorant]

The image forming material according to the exemplary embodiment of the present invention may contain a colorant so as to impart a color to the image forming material. The colorant may be a pigment or a dye, and a known colorant may be used. One kind of a colorant may be used alone, or two or more kinds of colorants may be used in combination.

[Other Components]

In the case where the image forming material according to the exemplary embodiment of the present invention is an electrophotographic toner, the image forming material may contain a release agent. The release agent includes, for example, a hydrocarbon-based wax; a natural wax such as carnauba wax, rice wax and candelilla wax; a synthetic or mineral/petroleum-based wax such as montan wax; and an ester-based wax such as fatty acid ester and montanic acid ester. One of these may be used, or two or more thereof may be used in combination.

In the case where the image forming material according to the exemplary embodiment of the present invention is an electrophotographic toner, the image forming material may contain a charge control agent, an offset-preventing agent, etc.

The charge control agent includes a control agent for positive charging and a control agent for negative charging. The control agent for positive charging includes, for example, a quaternary ammonium-based compound. The control agent for negative charging includes, for example, a metal complex of an alkylsalicylic acid, and a resin-type charge control agent containing a polar group.

The offset-preventing agent includes, for example, a low-molecular-weight polyethylene and a low-molecular-weight polypropylene.

In the case where the image forming material according to the exemplary embodiment of the present invention is an electrophotographic toner, an inorganic powder particle or an organic particle may be added as an external additive to the toner surface for the purpose of enhancing the flowability, powder storability, transfer performance, cleaning performance, etc.

The inorganic powder particle includes, for example, silica, alumina, titania, calcium carbonate, magnesium carbonate, calcium phosphate, and cerium oxide. Such an inorganic powder particle may be subjected to a known surface treatment.

The organic particle includes, for example, an emulsion polymer or soap-free polymer containing, as a constituent component, vinylidene fluoride, methyl methacrylate, styrene-methyl methacrylate, etc.

In the case where the image forming material according to the exemplary embodiment of the present invention is an ink for an inkjet printer, the ink may be in the form of an aqueous ink containing water. In this case, in order to prevent drying of the ink and improve the permeability, the ink may further contain a water-soluble organic solvent. The organic solvent includes, for example, polyhydric alcohols such as ethylene glycol, diethylene glycol, polyethylene glycol and glycerin; N-alkylpyrrolidones; esters such as ethyl acetate and amyl acetate; lower alcohols such as methanol, ethanol, propanol and butanol; and glycol ethers of ethylene oxide or propylene oxide adducts, etc. of methanol, butanol and phenol. One organic solvent may be used alone, or two or more organic solvents may be used in combination.

The organic solvent is selected by taking into consideration the hygroscopicity, moisture retentivity, solubility of the infrared absorber, permeability, viscosity of the ink, freezing point, etc. The content ratio of the organic solvent in the ink for an inkjet printer is preferably from 1 mass % to 60 mass %.

In the case where the image forming material according to the exemplary embodiment of the present invention is an ink for an inkjet printer, the ink may contain a known additive as an ink component so as to satisfy various conditions required of the system of an inkjet printer. The additive includes, for example, a pH adjuster, a specific resistance adjuster, an antioxidant, an antiseptic, a fungicide, and a metal sequestering agent.

In the case where the image forming material according to the exemplary embodiment of the present invention is an ink for an inkjet printer, the ink may contain a water-soluble resin, such as polyvinyl alcohol, polyvinylpyrrolidone, carboxymethyl cellulose, styrene-acrylic acid resin and styrene-maleic acid resin, to such an extent as not to cause clogging of a nozzle part or change in the ink discharge direction.

In the case where the image forming material according to the exemplary embodiment of the present invention is an ink for printing such as letterpress printing, offset printing, flexo printing, gravure printing or silk printing, the ink may be in the form of an oily ink containing a polymer or an organic solvent.

The polymer includes, for example, a natural resin such as protein, rubber, celluloses, shellac, copal, starch and rosin; a thermoplastic resin such as vinyl-based resin, acrylic resin, styrene-based resin, polyolefin-based resin and a novolak-type phenolic resin; and a thermosetting resin such as resol-type phenolic resin, urea resin, melamine resin, polyurethane resin, epoxy resin and unsaturated polyester.

The organic solvent includes the organic solvents exemplified above in the description of the ink for an inkjet printer.

In the case where the image forming material according to the exemplary embodiment of the present invention is an ink for printing such as letterpress printing, offset printing, flexo printing, gravure printing or silk printing, the ink may contain a known additive as an ink component so as to satisfy various conditions required. The additive includes, for example, a plasticizer, an anti-drying agent, a viscosity adjuster, a dispersant, and a solvent.

[Production Method of Electrophotographic Toner]

In the case where the image forming material according to the exemplary embodiment of the present invention is an electrophotographic toner, the production method of the toner includes a dry production method (for example, a kneading/grinding method) and a wet production method (for example, an aggregation/coalescence method, a suspension polymerization, and a dissolution suspension method).

In the case of producing the toner according to a known aggregation/coalescence method, a resin particle dispersion liquid having dispersed therein resin particles each containing an infrared absorber, at least either a carboxylic acid ester or a phosphoric acid ester (referred to as "esters"), and other components is prepared.

This preparation may be performed, for example, by applying a shear force with a disperser to a solution in which a dispersion medium (e.g., water, ethers, ketones, alcohols), a resin, an infrared absorber, esters and other components are mixed. For the purpose of further stabilizing the dispersed resin particles, a dispersant (for example, a water-soluble polymer, a surfactant or an inorganic salt) may be used.

In addition, the resin particles may be dispersed in a dispersion medium by a phase inversion emulsification method. The phase inversion emulsification method is a method where a resin to be dispersed is dissolved in a hydrophobic organic solvent in which the resin is soluble, a base is added to the organic continuous phase (O-phase) to effect neutralization, and water (W-phase) is then charged to cause phase inversion from W/O to O/W, thereby dispersing the resin as particles in an aqueous medium.

The amount of each of the infrared absorber and esters used for the preparation of the dispersion liquid may be from 0.05 parts by mass to 20 parts by mass, preferably from 0.1 parts by mass to 10 parts by mass, per 100 parts by mass of the resin. The volume average particle diameter of the infrared absorber-containing resin particles may be from 1 nm to 1,000 nm, preferably from 10 nm to 500 nm, more preferably from 50 nm to 200 nm.

<Image Forming Method>

An image forming method including a step of imparting an image forming material to the surface of a recording medium by using the image forming material according to the exemplary embodiment of the present invention, and a step of irradiating the image forming material imparted to the surface of a recording medium with light containing an infrared ray, thereby fixing the image forming material to a recording medium, is provided.

The light source for the light containing an infrared ray is not particularly limited, and a known light source such as halogen lamp, mercury lamp, infrared laser and rare gas-filled flash lamp may be employed. The irradiation energy per unit area is, for example, from 1.0 J/cm$^2$ to 10.0 J/cm$^2$.

The recording medium includes paper, a plastic plate, cloth, a metal plate, etc. The material quality and properties of the recording medium are preferably of the level capable of withstanding heat at the time of fixing.

The method for imparting the image forming material to a recording medium includes, for example, an electrophotographic system, an inkjet system, letterpress printing, offset printing, flexo printing, gravure printing and silk printing. From the standpoint of efficiently heating the image forming material on a recording medium by the infrared irradiation, it is preferred that a liquid (e.g., water) other than the image forming material is not imparted to a recording medium. Accordingly, the method for imparting the image forming material to a recording medium is preferably an electrophotographic system.

EXAMPLES

The present invention is described more specifically below by referring to Examples, but the present invention is not limited to these Examples by any means.

In the following description, unless otherwise indicated, the "parts" is on the mass basis.

In the following description, THF means tetrahydrofuran.

<Synthesis of Thiopyran-Based Squarylium>

[Synthesis of Compound A-01]

Compound A-01 is synthesized according to the following synthesis scheme. The structure of the intermediate product is confirmed by an NMR spectrum, a mass spectrum, etc.

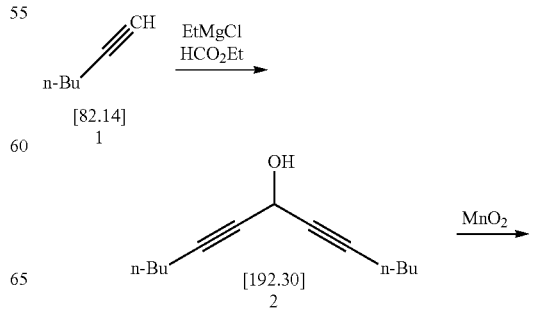

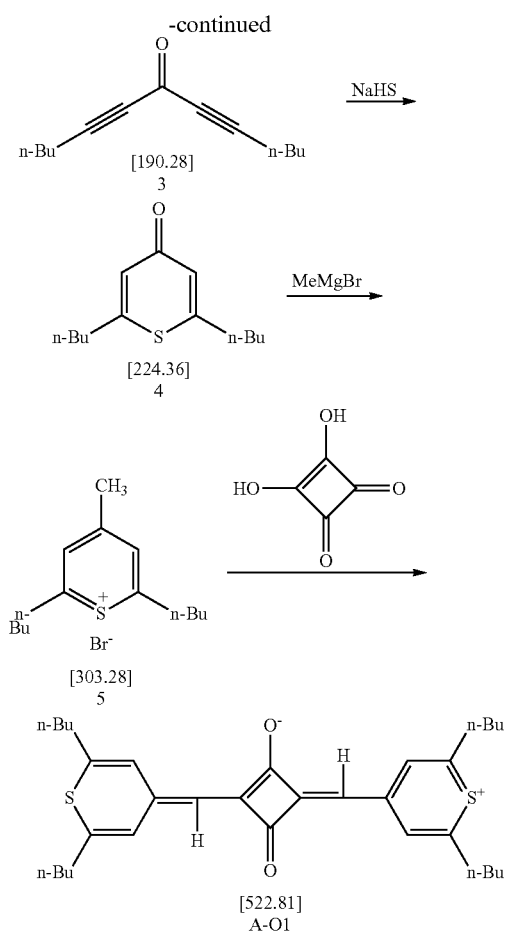

1. Synthesis of Intermediate 2
(trideca-5,8-diyn-7-ol)

A stirring seal, a Teflon (registered trademark)-made stirring bar, a pressure-equalizing dropping funnel, a nitrogen inlet tube and a thermometer were equipped to a 1-L three-neck flask to make up a reaction vessel (the nitrogen inlet tube and the thermometer are fixed to one port by utilizing a branch pipe). The inside of the reaction vessel is purged with nitrogen, and 254.3 g (0.515 mol) of a tetrahydrofuran 2M solution of ethylmagnesium chloride (Tokyo Chemical Industry Co., Ltd., 18%) is charged into the reaction vessel in a nitrogen atmosphere. The contents are cooled to 10° C. in an ice water bath, and 46.3 g (0.564 mol) (a slightly large amount in the anticipation that the Grignard reagent is contained somewhat in a large amount) of 1-hexyne (Tokyo Chemical Industry Co., Ltd., 97%) is added dropwise over about 40 minutes (temperature of reaction solution (hereinafter referred to as "inner temperature"): from 10° C. to 15° C.). After the completion of dropwise addition, the water bath is removed, and the solution is stirred at room temperature for 1.5 hours. Subsequently, 20.68 g (0.279 mol) of ethyl formate is added dropwise while cooling with an ice water bath (inner temperature: from 10° C. to 20° C.). After the completion of dropwise addition, the solution is stirred at room temperature for 30 minutes, and 115 ml (0.69 mol) of 6 N hydrochloric acid is added dropwise while cooling with an ice water bath (inner temperature: from 15° C. to 40° C.). After the completion of dropwise addition, the solution is stirred at room temperature for 30 minutes, and a solution obtained by dissolving 16.8 g (0.2 mol) of sodium hydrogencarbonate in 80 ml of water is slowly added dropwise. The organic (THF) layer is separated from the layer-separated reaction mixture after neutralization, concentrated under reduced pressure in a rotary evaporator and further vacuum-dried at 70° C. to obtain 45.8 g of a yellow-white liquid (P1). The aqueous layer (semisolid) is extracted three times with 100 ml of ethyl acetate, and the ethyl acetate extract is concentrated under reduced pressure in a rotary evaporator. The precipitated inorganic salt is removed by filtration under reduced pressure, and the residue is vacuum-dried at 70° C. to obtain 4.3 g of a yellow-white liquid (P2). The total amount of P1 and P2 was 50.1 g, and the crude yield based on ethylmagnesium chloride is 101%.

2. Synthesis of Intermediate 3
(trideca-5,8-diyn-7-one)

A Dean-Stark trap, a reflux condenser, a stirring seal and a Teflon (registered trademark)-made stirring bar are equipped to a 500-mL three-neck flask to make up a reaction vessel, and 47.06 g (244.7 mmol) of Intermediate 2 (unpurified) and 180 ml of cyclohexane are charged into the reaction vessel. Furthermore, 101 g (987 mmol) of manganese(IV) oxide powder (not activated, Kanto Chemical Co., Inc., first class, 85%) is added, and the mixture is stirred by a three-one motor and refluxed under heating for 2.7 hours. Water produced during the reaction is removed by azeotropic distillation. No remaining of Intermediate 2 is confirmed by thin-layer chromatography (Intermediate 2 and Intermediate 3 can be confirmed also by iodine coloration and an UV lamp, respectively). The reaction mixture is allowed to cool and then filtered under reduced pressure to obtain a yellow filtrate (F1). The solid obtained by filtration is transferred to another vessel, and an operation of adding about 100 ml of ethyl acetate and subjecting the mixture to ultrasonic dispersion (10 minutes) and filtration is repeated four times. The ethyl acetate extract liquid (F2) is mixed with F1, and the resulting solution is concentrated in a rotary evaporator and then with a vacuum pump to obtain 43 g of an orange-colored liquid. The crude yield is 92.4%. The orange-colored liquid is distillated under reduced pressure to obtain 34.9 g of a pale yellow liquid as the fraction of 145° C./9 mmHg (or from 162° C. to 169° C./18 mmHg). The distillation yield is 75%.

3. Synthesis of Intermediate 4
(2,6-di-n-butyl-4H-thiopyran-4-one)

A thermometer and a dropping funnel are equipped to a 300-mL three-neck flask to make up a reaction vessel, and 3.96 g (content: 70%, 49.5 mmol) of sodium hydrogen monosulfide n-hydrate (Wako Pure Chemical Industries, Ltd.) is added to 200 ml of 95% ethanol. After stirring at room temperature until dissolving the hydrate (about 15 minutes), the solution is cooled with ice water, and when the inner temperature reaches 5° C., a mixed solution containing 8.563 g (45 mmol) of Intermediate 3 and 18 ml of 95% ethanol is added dropwise little by little. The color of the liquid is changed from yellow to orange by the dropwise addition. Since the inner temperature rises due to heat generation, the dropwise addition is performed in the inner temperature range from 5° C. to 7° C. while adjusting the dropwise addition amount. The dropping funnel is flushed with 6 ml of 95% ethanol. The dropwise addition time is 32 minutes. The ice water bath is then removed, and the solution is stirred at room temperature (22° C.) with a natural temperature rise for 30 minutes. Subsequently, 300 ml of water is charged into the reaction solution, and ethanol is removed in a rotary evaporator (heating temperature: 35° C.). Thereafter, a common salt is added until reaching saturation, and liquid separation with ethyl acetate is performed three times to recover the organic phase (100 ml×3). The organic phase is washed twice with 15 ml of saturated ammonium chloride (the washing solution is confirmed to be at a pH of 7 by a pH test paper) and dried over magnesium sulfate. After the drying, the obtained organic layer is concentrated under reduced pressure to recover 10.1 g of a brown liquid (the crude yield is 100%). The UV spectrum of the liquid is measured, and it is revealed that the yield of the target compound is 66%. This liquid is distilled under reduced pressure at 6 torr. Fractional distillation starts at a bath temperature of 200° C., but since the initial distillate contains almost no fraction, main distillate is collected when the steam flow is increased, as a result, 6.16 g of a yellow liquid having a boiling point of 160° C. to 168° C. is distillated at a bath temperature of 205° C. to 215° C. The distillation yield is 61%.

4. Intermediate 5
(2,6-di-n-butyl-4-methylthiopyrylium bromide)

After placing a Teflon (registered trademark)-made stirring bar and 8.976 g (40 mmol) of Intermediate 4 in a 200-mL three-neck flask, a nitrogen inlet tube and a reflux condenser are attached thereto, followed by nitrogen purging. In a nitrogen atmosphere, 80 ml of anhydrous tetrahydrofuran is added by syringe, and 58.3 g (58.7 mmol) of a 1 M tetrahydrofuran solution of methylmagnesium bromide is added dropwise by syringe while stirring at room temperature. Since an exothermic reaction occurs, the temperature of the reaction solution rises to about 50° C. After the completion of dropwise addition, the reaction solution is heated with stirring and refluxed for 1 hour. In a nitrogen atmosphere, the reaction solution is allowed to cool and thereafter, a solution obtained by dissolving 17.5 g (178.7 mmol) of ammonium bromide in 23.3 g of water is added while cooling with an ice water bath. The reaction mixture is further stirred at room temperature for 18 minutes and after adding 50 ml of n-hexane, dried over sodium sulfate (7.0 g) for 16 hours. After the drying, an n-hexane/THF solution is drawn into the syringe cylinder, and the inorganic layer is washed with ethyl acetate (50 ml×3) to obtain an extract liquid. The n-hexane/THF solution and the extract liquid from the inorganic layer are mixed, and the mixture is concentrated under reduced pressure, then vacuum-dried and immediately subjected to a dye formation reaction. At this stage, 9.75 g of Intermediate 5 is obtained. The crude yield is 80.4%.

5. Synthesis of Compound A-01

In a nitrogen atmosphere, 9.75 g (32.1 mmol) of Intermediate 5 and 1.467 g (12.9 mmol) of squaric acid are dispersed in a mixed solvent of 50 ml of cyclohexane and 50 ml of isobutanol and after adding 267.7 mg (3.2 mmol) of pyridine (purity: 95%), the mixture is refluxed under heating for 2.5 hours. Thereafter, 25 ml of isobutanol is additionally added, and the reaction mixture is refluxed under heating for another 1.5 hours. Water produced during the reaction is removed by azeotropic distillation. The reaction mixture is allowed to cool and then filtered under reduced pressure, and sparingly soluble substances are removed by THF washing. The filtrate is concentrated in a rotary evaporator (heating temperature: from 30° C. to 55° C.) to remove the solvent, as a result, a dye crystal is precipitated. Thereafter, 100 ml of n-hexane is added to the crystal, and the mixture is subjected to ultrasonic dispersion (5 minutes) and then to filtration, washed with 60 ml of n-hexane and 100 ml of methanol, and vacuum-dried (about 55° C.) to obtain 3.564 g of a gold-brown crystal taking on a metallic luster (yield based on squaric acid: 53.0%). This crystal product has an HPLC purity of 98.2%.

6. Identification of Compound

The gold-brown crystal is identified by the infrared absorption spectrum (KBr tablet method), $^1$H-NMR spectrum, mass spectrum, and visible-infrared absorption spectrum. As a result, the gold-brown crystal is confirmed to have the molecular structure of Compound A-01. The identification data are set forth below, and FIG. 1 shows the molar extinction coefficient ($\epsilon$) spectrum.

Infrared Absorption Spectrum (KBr Tablet Method):

$\nu_{max}$=3030 (=C—H), 2956, 2931, 2872, 2860, 1724, 1603, 1591, 1566 (C=C ring), 1477, 1460, 1344, 1325, 1306, 1298, 1213, 1194, 1088 (C—O$^-$), 989, 829, 710 cm$^{-1}$.

$^1$H-NMR Spectrum (CDCl$_3$):

9.068 (s, 2H), 6.793 (s, 2H), 6.019 (s, 2H), 2.655 (t, J=7.80 Hz, 4H, CH$_2$), 2.551 (t, J=7.56 Hz, 4H, CH$_2$), 1.728 (m, 4H, CH$_2$), 1.625 (m, 4H, CH$_2$), 1.458-1.363 (m, 8H, CH$_2$), 0.982-0.927 (m, 12H, CH$_3$).

Mass Spectrum (FD):

m/z=523 (M$^+$, 100%)

Molar Extinction Coefficient ($\epsilon$) Spectrum:

Maximum absorption wavelength ($\lambda_{max}$)=810 nm (in THF)

Molar extinction coefficient ($\epsilon_{max}$) at maximum absorption wavelength=3.58×10$^5$ M$^{-1}$ cm$^{-1}$

[Synthesis of Compound A-04]

Compound A-04 is synthesized in the same manner as in the synthesis of Compound A-01 except for using 1-pentyne in place of 1-hexyne. The synthesized compound is identified as Compound A-04 by the infrared absorption spectrum (KBr tablet method), $^1$H-NMR spectrum, mass spectrum, and visible-infrared absorption spectrum. The identification data are set forth below, and FIG. 2 shows the molar extinction coefficient (E) spectrum.

Infrared Absorption Spectrum (KBr Tablet Method):

$\nu_{max}$=3030 (=C—H), 2962, 2931, 2872, 1722, 1605, 1568 (C=C ring), 1481, 1354, 1329, 1308, 1242, 1207, 1076 (C—O$^-$), 985, 827, 796, 710 cm$^{-1}$.

$^1$H-NMR Spectrum (CDCl$_3$):

9.073 (s, 2H), 6.796 (s, 2H), 6.018 (s, 2H), 2.626 (t, J=7.56 Hz, 4H, CH$_2$), 2.528 (t, J=7.56 Hz, 4H, CH$_2$), 1.789 (m, 4H, CH$_2$), 1.675 (m, 4H, CH$_2$), 1.040-0.965 (m, 12H, CH$_3$).

Mass Spectrum (FD):
m/z=467 (M+, 100%)
Molar Extinction Coefficient (ε) Spectrum:
Maximum absorption wavelength ($\lambda_{max}$)=809 nm (in THF)
Molar extinction coefficient ($\epsilon_{max}$) at maximum absorption wavelength=$3.60 \times 10^5$ M$^{-1}$ cm$^{-1}$

[Synthesis of Compound A-06]

Compound A-06 is synthesized in the same manner as in the synthesis of Compound A-01 except for using 1-heptyne in place of 1-hexyne. The synthesized compound is identified as Compound A-06 by the infrared absorption spectrum (KBr tablet method), $^1$H-NMR spectrum, mass spectrum, and visible-infrared absorption spectrum. The identification data are set forth below, and FIG. 3 shows the molar extinction coefficient (E) spectrum.

Infrared Absorption Spectrum (KBr Tablet Method):
$\nu_{max}$=3030 (=C—H), 2954, 2927, 2870, 2856, 1722, 1603, 1589, 1566 (C=C ring), 1462, 1352, 1329, 1306, 1209, 1184, 1092 (C—O$^-$), 1001, 914, 887, 715, 694, 640 cm$^{-1}$.

$^1$H-NMR Spectrum (CDCl$_3$):
9.068 (s, 2H), 6.793 (s, 2H), 6.019 (s, 2H), 2.655 (t, J=7.56 Hz, 4H, CH$_2$), 2.551 (t, J=7.56 Hz, 4H, CH$_2$), 1.728 (m, 4H, CH$_2$), 1.625 (m, 4H, CH$_2$), 1.458-1.150 (m, 16H, CH$_2$), 0.950-0.900 (m, 12H, CH$_3$).

Mass Spectrum (FD):
m/z=579 (M+, 100%)
Molar Extinction Coefficient (ε) Spectrum:
Maximum absorption wavelength ($\lambda_{max}$)=810 nm (in THF)
Molar extinction coefficient ($\epsilon_{max}$) at maximum absorption wavelength=$3.68 \times 10^5$ M$^{-1}$ cm$^{-1}$ <Study on Thermal Stability of Thiopyran-Based Squarylium Compound>

A pseudo-toner containing Compound A-01, A-04, A-06, A-19, A-20 or A-10 is produced, and the thermal stability and invisibility of each thiopyran-based squarylium compound are examined.

[Production of Pseudo-Toner Dispersion Liquid]

400 μl of a THF solution (concentration: 1 mg/ml) of the thiopyran-based squarylium compound and 800 μl of a THF solution (concentration: 10 mg/ml) of a toner resin (poly(styrene-n-butyl acrylate)) are mixed, and a half amount (600 μl) of the solution is suctioned by a micropipette and injected in a burst into 100 ml of distilled water previously added with 35 mg of potassium carbonate while stirring the distilled water at 400 rpm to perform reprecipitation. After 1 minute from the injection, a slurry where a thiopyran-based squarylium compound is dispersed in the resin is obtained. This slurry (pseudo-toner dispersion liquid) has a volume average particle diameter of 115 nm.

[Production of Latex Patch]

Using a glass filter having an inner diameter of 36 mm, 5.0 ml of the pseudo-toner dispersion liquid above is filtered through an MF-Millipore membrane filter (cellulose-mixed ester, produced by Merck, Ltd., model number: VMWP) having a pore size of 50 nm and air-dried. The solid material after drying is a latex patch in which the amount of toner applied is 0.21 g/m$^2$ and the amount of the thiopyran-based squarylium compound per unit area is 0.01 g/m$^2$ (corresponding to 4.76 mass %). This latex patch is measured for the reflection spectrum by a spectrophotometer (U-4100, manufactured by Hitachi, Ltd.), and the infrared absorption factor K11(%) at the maximum absorption wavelength (822 nm) of the latex patch is determined.

[Production of Latex Patch by Laser Fixing]

An electrophotographic image forming apparatus (DocuCenter Color 2220, manufactured by Fuji Xerox Co., Ltd.) is prepared, where the laser light of the optical fixing device is set at a wavelength of 810 nm and the irradiation energy is set to 1.5 J/cm$^2$.

Using a glass filter having an inner diameter of 36 mm, 5.0 ml of the pseudo-toner dispersion liquid obtained above is filtered through the MF-Millipore membrane filter above and air-dried. The solid material after drying is optically fixed on the membrane filter above by the optical fixing device above to produce a latex patch in which the amount of toner applied is 0.21 g/m$^2$ and the amount of the thiopyran-based squarylium compound per unit area is 0.01 g/m$^2$ (corresponding to 4.76 mass %). This latex patch is measured for the reflection spectrum by a spectrophotometer (U-4100, manufactured by Hitachi, Ltd.), and the infrared absorption factor K12(%) at the maximum absorption wavelength (822 nm) of the latex patch is determined.

[Evaluation]

[Thermal Stability]

The thermal stability of the thiopyran-based squarylium compound is decided by the ratio (K12/K11) between the infrared absorption factor K12 and the infrared absorption factor K11, according to the following criteria for judgment. The results obtained are shown in Table 1.

—Criteria for Judgment—
A: K12/K11 is 0.95 or more.
B: K12/K11 is from 0.9 to less than 0.95.
C: K12/K11 is less than 0.9.

Incidentally, when K12/K11 is less than 0.95, the decomposition ratio of the infrared absorber at the time of optical fixing becomes high and a volatile sulfur compound is likely to be generated. The volatile sulfur compound is a substance of which load in vivo or on the environment is concerned, and therefore, in view of the safety of operation at the site for performing the optical fixing and the effect on the environment, K12/K11 is preferably 0.95 or more, though this may vary depending on the conditions of optical fixing.

[Invisibility]

The latex patch fixed on paper by laser is measured for L* value, a* value and b* value in the CIE 1976 L*a*b* color space by using a reflection spectral densitometer (X-Rite 939, manufactured by X-Rite Inc.), the color difference ΔE is calculated based on the following formula, and the invisibility is decided according to the following criteria for judgment. The results obtained are shown in Table 1. As to the color difference ΔE, a smaller value indicates less visible, that is, higher invisibility.

$$\Delta E = \sqrt{(L_1-L_2)^2 + (a_1-a_2)^2 + (b_1-b_2)^2}$$

wherein $L_1$, $a_1$ and $b_1$ are L* value, a* value and b* value of a latex patch (amount applied: 0.2 g/m$^2$) formed on the MF-Millipore membrane filter above by the same method using the toner resin (poly(styrene-n-butyl acrylate)) above, and $L_2$, $a_2$ and $b_2$ are L* value, a* value and b* value of a latex patch by the pseudo-toner.

—Criteria for Judgment—
A: The color difference ΔE is less than 3.
B: The color difference ΔE is from 3 to less than 6.
C: The color difference ΔE is from 6 to less than 10.
D: The color difference ΔE is 10 or more.

TABLE 1

| Compound | Thiopyran-Based Squarylium Compound Chemical Structure | $\lambda_{max}$ [nm] (in THF) | $\epsilon_{max}$ [M$^{-1}$cm$^{-1}$] (in THF) | Thermal Stability K12/K11 | Judgment | Invisibility Color Difference ΔE | Judgment |
|---|---|---|---|---|---|---|---|
| A-01 | | 810 | 3.58 × 10$^5$ | 0.98 | A | 2.5 | A |
| A-04 | | 809 | 3.60 × 10$^5$ | 0.99 | A | 2.5 | A |
| A-06 | | 810 | 3.68 × 10$^5$ | 0.97 | A | 2.6 | A |
| A-19 | | 812 | 3.50 × 10$^5$ | 0.94 | B | 2.8 | A |
| A-20 | | 817 | 3.47 × 10$^5$ | 0.93 | B | 2.9 | A |
| A-10 | | 810 | 3.52 × 10$^5$ | 0.89 | C | 3.3 | B |

It is seen from the results shown in Table 1 that Compounds A-01, A-04 and A-06 are excellent in thermal stability at the time of light energy absorption and associated heat generation, compared with Compounds A-19, A-20 and A-10.

Example 1

Production of Pseudo-Toner Dispersion Liquid

400 µl of a THF solution (concentration: 1 mg/ml) of an infrared absorber (Compound A-10), 200 µl of a THF solution (concentration: 2 mg/ml) of di(2-ethylhexyl) phthalate (DEHP), and 800 µl of a THF solution (concentration: 10 mg/ml) of a toner resin (polyester resin: a polycondensate of terephthalic acid/fumaric acid/bisphenol A ethylene oxide 2-mol adduct/bisphenol A propylene oxide 2-mol adduct=30 parts by mol/70 parts by mol/20 parts by mol/80 parts by mol) are mixed, and a half amount (700 µl) of the solution is suctioned by a micropipette and injected in a burst into 100 ml of distilled water previously added with 35 mg of potassium carbonate while stirring the distilled water at 400 rpm to perform reprecipitation. After 1 minute from the injection, a slurry where the infrared absorber and DEHP are dispersed in the resin is obtained. This slurry (pseudo-toner dispersion liquid) has a volume average particle diameter of 95 nm.

[Production of Latex Patch]

Using a glass filter having an inner diameter of 36 mm, 5.0 ml of the pseudo-toner dispersion liquid above is filtered through an MF-Millipore membrane filter (cellulose-mixed ester, produced by Merck, Ltd., model number: VMWP) having a pore size of 50 nm and air-dried. The solid material after drying is thermocompression-bonded (120° C.) on the membrane filter above to produce a latex patch in which the amount of toner applied is 0.22 g/m² and the amount of the infrared absorber per unit area is 0.01 g/m² (corresponding to 4.55 mass %).

[Evaluation]

[Degree of Enhancement of Infrared Absorption Factor]

The latex patch obtained above is measured for the reflection spectrum by a spectrophotometer (U-4100, manufactured by Hitachi, Ltd.), and the infrared absorption factor K1(%) at the maximum absorption wavelength (in Example 1, 821 nm) of the latex patch is determined.

As a reference sample for judging the degree of enhancement of the infrared absorption factor, a pseudo-toner dispersion liquid and a latex patch are produced in the same manner as above without using a THF solution of DEHP, and the infrared absorption factor K0(%) at the maximum absorption wavelength (in Example 1, 821 nm) of the latex patch is determined by the same method as above.

The degree of enhancement of the infrared absorption factor is decided by the ratio (K1/K0) between the infrared absorption factor K1 and the infrared absorption factor K0, according to the following criteria for judgment. The results obtained are shown in Table 2.

—Criteria for Judgment—
A: K1/K0 is 1.15 or more.
B: K1/K0 is from 1.1 to less than 1.15.
C: K1/K0 is from 1.05 to less than 1.1.
D: K1/K0 is less than 1.05.

[Invisibility]

The latex patch obtained above is measured for L* value, a* value and b* value in the CIE 1976 L*a*b* color space by using a reflection spectral densitometer (X-Rite 939, manufactured by X-Rite Inc.), the color difference ΔE is calculated based on the following formula, and the invisibility is decided according to the following criteria for judgment. The results obtained are shown in Table 2. As to the color difference ΔE, a smaller value indicates less visible, that is, higher invisibility.

$$\Delta E = \sqrt{(L_1-L_2)^2 + (a_1-a_2)^2 + (b_1-b_2)^2}$$

wherein $L_1$, $a_1$ and $b_1$ are L* value, a* value and b* value of a latex patch (amount applied: 0.2 g/m²) formed on the MF-Millipore membrane filter above by the same method using the toner resin (polyester resin) above, and $L_2$, $a_2$ and $b_2$ are L* value, a* value and b* value of the latex patch of Example.

—Criteria for Judgment—
A: The color difference ΔE is less than 3.
B: The color difference ΔE is from 3 to less than 6.
C: The color difference ΔE is from 6 to less than 10.
D: The color difference ΔE is 10 or more.

Examples 2 to 24

Pseudo-toner dispersion liquids and latex patches are produced and evaluated in the same manner as in Example 1 except that the kinds and used amounts of the infrared absorber and esters are changed as shown in Table 2. The results obtained are shown in Table 2.

Examples 25 and 26

Pseudo-toner dispersion liquids and latex patches are produced and evaluated in the same manner as in Example 1 except that a THF solution of the toner resin (polyester resin) is changed to a THF solution (concentration: 10 mg/ml) of poly(styrene-n-butyl acrylate). The results obtained are shown in Table 2.

Comparative Examples 1 to 13

Pseudo-toner dispersion liquids and latex patches are produced and evaluated in the same manner as in Example 1 except that the kinds and used amounts of the infrared absorber and esters are changed as shown in Table 2. The results obtained are shown in Table 2. Structural formulae of the infrared absorbers for comparison are illustrated below.

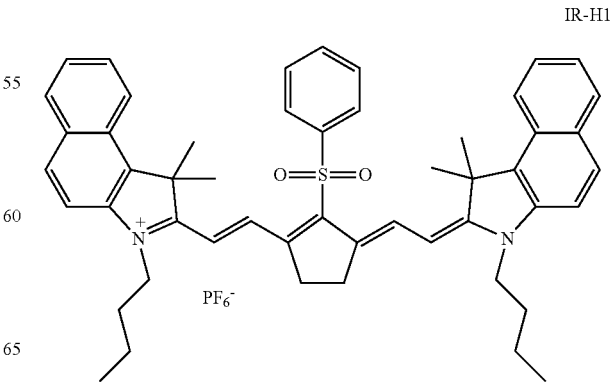

IR-H1

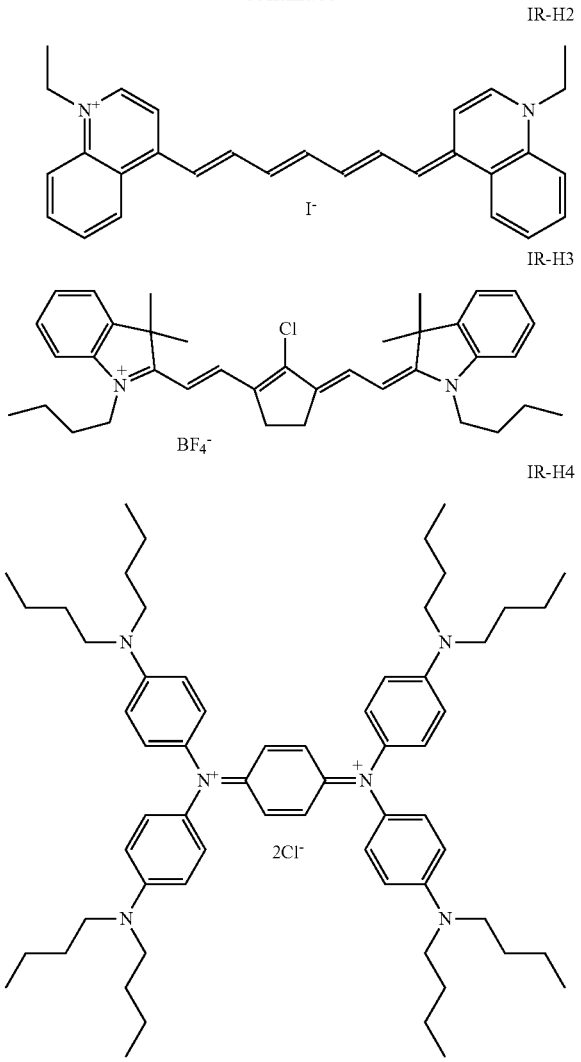

The maximum absorption wavelength ($\lambda_{max}$) and the molar extinction coefficient ($\epsilon_{max}$) at the maximum absorption wavelength of the infrared absorber used in each of Examples and Comparative Examples are measured and found to be as follows.

A-01: $\lambda_{max}$ 810 nm (in THF), $\epsilon_{max}$ 3.58×10$^5$ M$^{-1}$ cm$^{-1}$
A-05: $\lambda_{max}$ 812 nm (in THF), $\epsilon_{max}$ 3.68×10$^5$
A-09: $\lambda_{max}$ 814 nm (in THF), $\epsilon_{max}$ 3.89×10$^5$ M$^{-1}$ cm$^{-1}$
A-10: $\lambda_{max}$ 810 nm (in THF), $\epsilon_{max}$ 3.52×10$^5$ M$^{-1}$ cm$^{-1}$
A-13: $\lambda_{max}$ 908 nm (in THF), $\epsilon_{max}$ 2.69×10$^5$ M$^{-1}$ cm$^{-1}$
A-16: $\lambda_{max}$ 865 nm (in THF), $\epsilon_{max}$ 2.46×10$^5$ M$^{-1}$ cm$^{-1}$
B-02: $\lambda_{max}$ 813 nm (in THF), $\epsilon_{max}$ 1.85×10$^5$ M$^{-1}$ cm$^{-1}$
B-04: $\lambda_{max}$ 815 nm (in THF), $\epsilon_{max}$ 1.59×10$^5$ M$^{-1}$ cm$^{-1}$
IR-H1: $\lambda_{max}$ 909 nm (in methanol), $\epsilon_{max}$ 2.55×10$^5$ M$^{-1}$ cm$^{-1}$
IR-H2: $\lambda_{max}$ 928 nm (in methanol), $\epsilon_{max}$ 1.49×10$^5$ M$^{-1}$ cm$^{-1}$
IR-H3: $\lambda_{max}$ 805 nm (in methanol), $\epsilon_{max}$ 3.13×10$^5$ M$^{-1}$ cm$^{-1}$
IR-H4: $\lambda_{max}$ 1068 nm (in acetone), $\epsilon_{max}$ 6.40×10$^4$ M$^{-1}$ cm$^{-1}$ In Table 2, the abbreviations of esters and comparative compounds stand for the following compounds.

DEHP: Di(2-ethylhexyl) phthalate
DIDP: Diisodecyl phthalate
DINP: Diisononyl phthalate
DNP: Dinonyl phthalate
DBP: Dibutyl phthalate
DEHA: Di(2-ethylhexyl) adipate
DINA: Diisononyl adipate
DEHS: Di(2-ethylhexyl) sebacate
TOTM: Tris(2-ethylhexyl)trimellitate
ATBC: Tributyl acetylcitrate
TCP: Tricresyl phosphate
EHO: (2-Ethylhexyl) octanoate
ESBO: Epoxidized soybean oil
ELSO: Epoxidized linseed oil

TABLE 2

| | Infrared Absorber | | Esters or Comparative Compound | | Degree of Enhancement of Infrared Absorption Factor | | Invisibility Color Difference | |
|---|---|---|---|---|---|---|---|---|
| | Kind | Amount per 100 Parts of Resin [parts] | Kind | Amount per 100 Parts of Resin [parts] | K1/K0 | Judgment | ΔE | Judgment |
| Example 1 | A-10 | 5 | DEHP | 5 | 1.17 | A | 2.8 | A |
| Example 2 | A-10 | 5 | DEHP | 2.5 | 1.18 | A | 2.8 | A |
| Example 3 | A-10 | 5 | DEHP | 10 | 1.15 | A | 2.8 | A |
| Example 4 | A-09 | 5 | DEHP | 5 | 1.17 | A | 2.7 | A |
| Example 5 | A-13 | 5 | DEHP | 5 | 1.16 | A | 2.9 | A |
| Example 6 | A-16 | 5 | DEHP | 5 | 1.16 | A | 2.9 | A |
| Example 7 | A-01 | 5 | DEHP | 5 | 1.17 | A | 2.8 | A |

TABLE 2-continued

| | Infrared Absorber | | Esters or Comparative Compound | | Degree of Enhancement of Infrared Absorption Factor | | Invisibility Color Difference | |
|---|---|---|---|---|---|---|---|---|
| | | Amount per 100 Parts of Resin | | Amount per 100 Parts of Resin | | | | |
| | Kind | [parts] | Kind | [parts] | K1/K0 | Judgment | ΔE | Judgment |
| Example 8 | A-01 | 5 | DIDP | 5 | 1.17 | A | 2.8 | A |
| Example 9 | A-01 | 5 | DINP | 5 | 1.16 | A | 2.9 | A |
| Example 10 | A-01 | 5 | DNP | 5 | 1.14 | B | 3.5 | B |
| Example 11 | A-01 | 5 | DBP | 5 | 1.12 | B | 3.7 | B |
| Example 12 | A-01 | 5 | DEHS | 5 | 1.18 | A | 2.7 | A |
| Example 13 | A-01 | 5 | TOTM | 5 | 1.20 | A | 2.7 | A |
| Example 14 | A-05 | 5 | ATBC | 5 | 1.15 | A | 2.9 | A |
| Example 15 | A-10 | 5 | TCP | 5 | 1.12 | B | 4.0 | B |
| Example 16 | A-10 | 5 | EHO | 5 | 1.14 | B | 3.5 | B |
| Example 17 | A-13 | 5 | DBP | 5 | 1.12 | B | 3.9 | B |
| Example 18 | A-16 | 5 | DNP | 5 | 1.13 | B | 3.7 | B |
| Example 19 | B-02 | 5 | DEHP | 5 | 1.15 | A | 2.9 | A |
| Example 20 | B-02 | 8 | DINA | 8 | 1.15 | A | 2.9 | A |
| Example 21 | B-04 | 5 | DEHP | 5 | 1.15 | A | 2.9 | A |
| Example 22 | B-04 | 5 | DEHA | 5 | 1.15 | A | 2.9 | A |
| Example 23 | B-04 | 5 | TCP | 5 | 1.11 | B | 4.1 | B |
| Example 24 | B-04 | 5 | EHO | 5 | 1.13 | B | 3.8 | B |
| Example 25 | A-10 | 5 | DEHP | 5 | 1.17 | A | 2.8 | A |
| Example 26 | B-04 | 5 | DEHP | 5 | 1.16 | A | 2.9 | A |
| Comparative Example 1 | A-10 | 5 | ESBO | 5 | 1.08 | C | 4.5 | B |
| Comparative Example 2 | A-10 | 5 | ELSO | 5 | 1.08 | C | 4.7 | B |
| Comparative Example 3 | IR-H1 | 5 | DEHP | 5 | 1.07 | C | 5.6 | B |
| Comparative Example 4 | IR-H2 | 5 | DEHA | 5 | 1.06 | C | 5.9 | B |
| Comparative Example 5 | IR-H3 | 5 | DEHS | 5 | 1.07 | C | 5.4 | B |
| Comparative Example 6 | IR-H4 | 5 | TOTM | 5 | 1.05 | C | 8.0 | C |
| Comparative Example 7 | IR-H1 | 5 | ATBC | 5 | 1.07 | C | 5.7 | B |
| Comparative Example 8 | IR-H1 | 5 | TCP | 5 | 1.05 | C | 5.9 | B |
| Comparative Example 9 | IR-H1 | 5 | EHO | 5 | 1.06 | C | 5.8 | B |
| Comparative Example 10 | IR-H1 | 5 | ESBO | 5 | 0.99 | D | 9.0 | C |
| Comparative Example 11 | IR-H2 | 5 | ELSO | 5 | 0.98 | D | 9.5 | C |
| Comparative Example 12 | IR-H3 | 5 | ESBO | 5 | 0.99 | D | 8.5 | C |
| Comparative Example 13 | IR-H4 | 5 | ELSO | 5 | 0.97 | D | 12.0 | D |

It is seen from the results shown in Table 2 that in Examples of the present invention, the infrared absorption factor is enhanced by virtue of containing a carboxylic acid ester or a phosphoric acid ester.

What is claimed is:

1. A composition, comprising:
a dispersion liquid having toner resin particles dispersed therein, each toner resin particle having dispersed therein:
an infrared absorber as an inner salt, and
at least either a carboxylic acid ester or a phosphoric acid ester,
wherein the infrared absorber as an inner salt is a compound represented by the following formula (A):

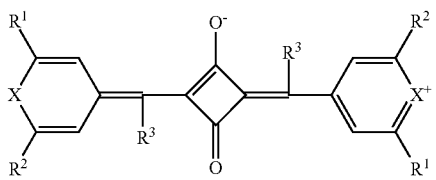

Formula (A)

wherein in formula (A), each of $R^1$ and $R^2$ independently represents an alkyl group or an aryl group, $R^3$ represents a hydrogen atom or an aliphatic group, and X represents an oxygen atom or a sulfur atom.

2. The composition according to claim 1,
wherein the infrared absorber as an inner salt is a thiopyran-based squarylium compound represented by the following formula (1):

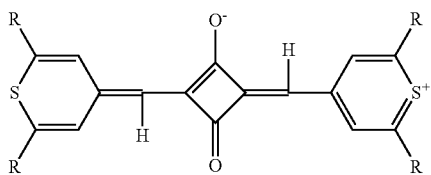

Formula (1)

wherein in formula (1), R represents a n-propyl group, a n-butyl group or a n-pentyl group.

3. The composition according to claim 1, wherein a volume average particle diameter of the toner resin particles is from 1 nm to 1,000 nm.

4. The composition according to claim 1, wherein a volume average particle diameter of the toner resin particles is from 50 nm to 200 nm.

5. The composition according to claim 1, wherein a content of the infrared absorber is from 0.05 parts by mass to 20 parts by mass per 100 parts by mass of the toner resin, and a total content of the carboxylic acid ester and phosphoric acid ester is from 0.05 parts by mass to 20 parts by mass per 100 parts by mass of the toner resin.

6. The composition according to claim 1, wherein a content of the infrared absorber is from 0.1 parts by mass to 10 parts by mass per 100 parts by mass of the toner resin, and a total content of the carboxylic acid ester and phosphoric acid ester is from 0.1 parts by mass to 10 parts by mass per 100 parts by mass of the toner resin.

7. A composition comprising:
an infrared absorber as an inner salt,
at least either a carboxylic acid ester or a phosphoric acid ester, and
a thermoplastic resin,
wherein the infrared absorber as an inner salt is a compound represented by the following formula (A):

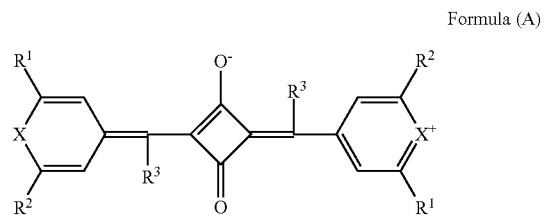

Formula (A)

wherein in formula (A), each of $R^1$ and $R^2$ independently represents an alkyl group or an aryl group, $R^3$ represents a hydrogen atom or an aliphatic group, and X represents an oxygen atom or a sulfur atom.

8. The composition according to claim 7,
wherein the infrared absorber as an inner salt is a thiopyran-based squarylium compound represented by the following formula (1):

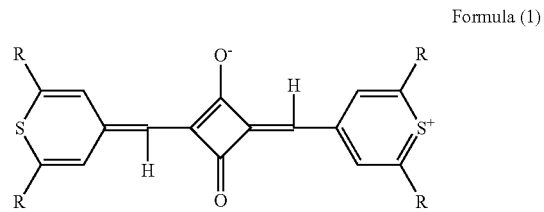

Formula (1)

wherein in formula (1), R represents a n-propyl group, a n-butyl group or a n-pentyl group.

* * * * *